United States Patent
Geddes

(10) Patent No.: US 8,679,402 B2
(45) Date of Patent: *Mar. 25, 2014

(54) MICROWAVE ACCELERATED ASSAYS

(71) Applicant: Chris D. Geddes, Bel-Air, MD (US)

(72) Inventor: Chris D. Geddes, Bel-Air, MD (US)

(73) Assignee: University of Maryland, Baltimore County, Baltimore, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/686,031

(22) Filed: Nov. 27, 2012

(65) Prior Publication Data

US 2013/0084628 A1    Apr. 4, 2013

Related U.S. Application Data

(60) Continuation of application No. 13/267,221, filed on Oct. 6, 2011, now Pat. No. 8,318,087, which is a division of application No. 11/719,731, filed as application No. PCT/US2005/042050 on Nov. 21, 2005, now Pat. No. 8,034,633.

(60) Provisional application No. 60/629,822, filed on Nov. 19, 2004, provisional application No. 60/640,290, filed on Dec. 30, 2004, provisional application No. 60/707,083, filed on Aug. 10, 2005.

(51) Int. Cl.
*A61L 2/00* (2006.01)
*C12M 1/34* (2006.01)
*G01N 33/553* (2006.01)

(52) U.S. Cl.
USPC ............... 422/21; 435/287.2; 436/525

(58) Field of Classification Search
USPC ............... 422/21; 435/287.2; 436/525
See application file for complete search history.

(56) References Cited

U.S. PATENT DOCUMENTS

| | | |
|---|---|---|
| 5,017,009 A | 5/1991 | Schutt et al. |
| 5,449,918 A | 9/1995 | Krull et al. |
| 5,741,462 A | 4/1998 | Nova et al. |
| 5,866,433 A | 2/1999 | Schalkhammer et al. |
| 6,515,040 B1 | 2/2003 | Scola et al. |
| 7,253,452 B2 | 8/2007 | Steckel et al. |
| 7,348,182 B2 | 3/2008 | Martin et al. |
| 7,351,590 B2 | 4/2008 | Martin |
| 7,718,445 B2 | 5/2010 | Martin |

(Continued)

FOREIGN PATENT DOCUMENTS

| | | |
|---|---|---|
| WO | WO 89/09408 | 10/1989 |
| WO | WO 2004/024191 | 3/2004 |
| WO | WO 2006/074130 | 7/2006 |

OTHER PUBLICATIONS

Bange, A., Halsall, H. B., and Heineman, W. R. 2005. Microfluidic immunosensor systems. *Biosens. Bioelectron.* 20(12):2488-2503.

(Continued)

*Primary Examiner* — Lore Jarrett
(74) *Attorney, Agent, or Firm* — Marianne Fuierer; Moore & Van Allen, PLLC

(57) ABSTRACT

The present invention provides for increasing fluorescence detection in surface assay systems while increasing kinetics of a bioreaction therein by providing low-power microwaves to irradiate metallic materials within the system in an amount sufficient to increase heat thereby affecting the kinetics of a bioreaction therein.

13 Claims, 27 Drawing Sheets

(56) References Cited

U.S. PATENT DOCUMENTS

| | | | |
|---|---|---|---|
| 8,034,633 B2* | 10/2011 | Geddes | 436/525 |
| 8,318,087 B2* | 11/2012 | Geddes | 422/21 |
| 2003/0082633 A1 | 5/2003 | Martin et al. | |
| 2003/0228682 A1 | 12/2003 | Lakowicz et al. | |
| 2004/0039158 A1 | 2/2004 | Lakowicz et al. | |
| 2004/0160606 A1 | 8/2004 | Lakowicz et al. | |
| 2005/0053974 A1 | 3/2005 | Lakowicz et al. | |
| 2005/0202464 A1 | 9/2005 | Lakowicz et al. | |
| 2006/0147927 A1* | 7/2006 | Geddes et al. | 435/6 |
| 2006/0256331 A1 | 11/2006 | Lakowicz et al. | |
| 2007/0020182 A1 | 1/2007 | Geddes et al. | |
| 2007/0269826 A1 | 11/2007 | Geddes | |
| 2008/0096281 A1 | 4/2008 | Geddes | |
| 2008/0215122 A1 | 9/2008 | Geddes | |
| 2009/0004461 A1 | 1/2009 | Geddes et al. | |
| 2009/0022766 A1 | 1/2009 | Geddes | |
| 2012/0238035 A1* | 9/2012 | Geddes | 436/501 |

OTHER PUBLICATIONS

Gosling, J. P. 1990. A decade of development in immunoassay methodology. *Clin. Chem.*, 36(8): 1408-1427.

Davidson, R. S.; Hilchenbach, M. M. 1990. The use of fluorescent probes in immunochemistry. *Photochem. Photobiol.*, 52(2): 431-438.

Schweitzer, B.; Kingsmore, S. F. 2002. Measuring proteins on microarrays. *Curr. Opin. Biotechnol.*, 13(1): 14-19.

Diamandis, E. P. 1988 Immunoassays with time-resolved fluorescence spectroscopy—principles and applications. *Clin. Biochem.*, 21(3): 139-150.

Khosravi, M.; Diamandis, E. P. 1987 Immunofluorometry of choriogonadotropin by time-resolved fluorescence spectroscopy, with a new europium chelate as label. *Clin. Chem.*, 33(11): 1993-1999.

Ullman, E. F.; Schwarzberg, M.; Rubenstein K. E. 1976. Fluorescent excitation transfer immunoassay—general method for determination of antigens. *J. Biol. Chem.*, 251(14): 4172-4178.

Ozinskas, A. J.; Malak, H.; Joshi, J.; Szmacinski, H.; Britz, J.; Thompson, R. B. Koen, P. A. Lakowicz, J. R. 1993. Homogenous model immunoassay of thyroxine by phase-modulation fluorescence spectroscopy. *Anal. Biochem.*, 213(2): 264-270.

Lakowicz, J. R; Maliwal, B.; Ozinskas, A. J.; Thompson, R. B. 1993. Fluorescence lifetime energy-transfer immunoassay quantified by phase-modulation fluorometry. *Sensors and Actuators B*, 12(1): 65-70.

Dandlike, W. B.; Saussure, V. A. 1970. Fluorescence polarization in immunochemistry. *Immunochemistry*, 7(9): 799-828.

Spencer, R. D.; Toledo, F. B.; Williams, B. T.; Yoss, N. L. 1973. Design, construction, and 2 applications for an automated flow-cell polarization fluorometer with digital read out—enzyme-inhibitor (antitrypsin) assay and antigen-antibody (insulin-insulin antiserum) assay. *Clin. Chem.*, 19(8): 838-844.

Aslan, K.; Gryczynski I.; Malicka J.; Matveeva E.; Lakowicz, J.R.; Geddes, C.D. 2005. Metal-enhanced fluorescence: an emerging tool in biotechnology. *Curr. Opin. Biotechnol.*, 16(1), 55-62.

Lakowicz J. R. (2001). Radiative decay engineering: Biophysical and biomedical applications. *Anal. Biochem.*, 298(1) 1-24.

Lakowicz J. R., Shen Y., D'Auria S., Malicka J., Fang J., Grcyzynski Z.and Gryczynski I. (2002). Radiative decay engineering 2. Effects of silver island films on fluorescence intensity, lifetimes, and resonance energy transfer. *Anal. Biochem.*, 301(2) 261-277.

Lakowicz J.R.; Shen Y.; Gryczynski Z.; D'Auria S.; Gryczynski I. 2001. Intrinsic fluorescence from DNA can be enhanced by metallic particles. *Biochem. Biophys. Res. Com.*, 286(5): 875-879.

Malicka J.; Gryczynski I.; Lakowicz J.R. 2003. DNA hybridization assays using metal-enhanced fluorescence. *Biochem. Biophys. Res. Com.*, 306(1): 213-218.

Lakowicz J.R.; Malicka J.; D'Auria S.; Gryczynski I. 2003. Release of the self-quenching of fluorescence near silver metallic surfaces. *Anal. Biochem.* 320(1): 13-20.

Aslan, K.; Lakowicz, J.R.; Szmacinski, H.; Geddes, C.D. 2005. Enhanced ratiometric pH sensing using SNAFL-2 on silver island films: Metal-Enhanced Fluorescence Sensing. *J. Fluorescence*, 15(1): 37-40.

Malicka, J.; Gryczynski, I.; Geddes, C. D.; Lakowicz, J. R. 2003. Metal-enhanced emission from indocyanine green: a new approach to in vivo imaging. *J. Biomed. Opt.*, 8(3): 472-478.

Geddes C. D., Cao H., Gryczynski I., Gryczynski Z., Fang J., and Lakowicz J. R. (2003). Metal-enhanced fluorescence due to silver colloids on a planar surface: potential applications of indocyanine green to in vivo imaging. *J. Phys. Chem. A*, 107(28) 3443-3449.

Aslan, K.; Lakowicz, J.R.; Geddes, C.D. 2005. Rapid deposition of triangular silver nanoplates on planar surfaces: application to metal-enhanced fluorescence. *J. Phys. Chem. B.*, 109: 6247-6251.

Aslan, K.; Leonenko, Z.; Lakowicz, J. R.; Geddes, C. D. 2005. Fast and slow deposition of silver nanorods on planar surfaces: application to metal-enhanced fluorescence. *J. Phys. Chem. B.*, 109(8): 3157-3162.

Parfenov, A.; Gryczynski, I.; Malicka, J.; Geddes, C. D.; Lakowicz, J. R. 2003. Enhanced fluorescence from fluorophores on fractal silver surfaces. *J. Phys. Chem. B.*, 107(34): 8829-8833.

Geddes C.D.; Parfenov, A.; Lakowicz, J.R. (2003). Photodeposition of silver can result in metal-enhanced fluorescence. *Applied Spectroscopy*, 57(5), 526-531.

Geddes, C.D.; Parfenov, A.; Roll, D.; Fang, J.; Lakowicz, J. R. (2003) Electrochemical and laser deposition of silver for use in metal-enhanced fluorescence. *Langmuir*, 19(15), 6236-6241.

Aslan, K.; Badugu, R.; Lakowicz, J.R.; Geddes, C.D. 2005. Metal-enhanced fluorescence from plastic substrates. *J. Fluorescence*, 15(2): 99-104.

Geddes, C.D.; Parfenov, A.; Roll, D.; Gryczynski, I.; Malicka, J.; Lakowicz, J. R. 2004. Roughened silver electrodes for use in metal-enhanced fluorescence. *Spectrochimica Acta Part A*, 60(8-9), 1977-1982.

Geddes C. D. and Lakowicz J. R. (2002). Metal-enhanced fluorescence. *J. Fluorescence*, 12(2) 121-129.

Lakowicz, J. R. 2004. Radiative decay engineering 3. Surface plasmon-coupled directional emission. *Anal. Biochem.* 324:153-169.

Matveeva, E.; Gryczynski Z.; Malicka, J.; Gryczynski, I.; Lakowicz, J.R. 2004. Metal-enhanced fluorescence immunoassays using total internal reflection and silver island-coated surfaces. *Analytical Biochemistry*, 334(2): 303-311.

Sridar, V. 1998. Microwave radiation as a catalyst for chemical reactions. *Current Science*, 74(5): 446-450.

Caddick, S. 1995. Microwave-assisted organic-reactions. *Tetrahedron*, 51(38): 10403-10432.

Lin, J.C.; Yuan, P.M.K.; Jung, D.T. 1998 Enhancement of anticancer drug delivery to the brain by microwave induced hyperthermia. *Bioelectrochemistry and Bioenergetics*, 47(2): 259-264.

Rhodes, A.; Jasani, B.; Balaton, A. J.; Barnes, D.M. ; Anderson, E. ; Bobrow, L. G.; Miller, K. D. 2001. Study of interlaboratory reliability and reproducibility of estrogen and progesterone receptor assays in Europe—Documentation of poor reliability and identification of insufficient microwave antigen retrieval time as a major contributory element of unreliable assays. *American J. Clinical Pathology*, 115 (1): 44-58.

Van Triest, B.; Loftus, B. M.; Pinedo, H. M.; Backus, H. H. J.; Schoenmakers, P.; Telleman F. 2000. Thymidylate synthase expression in patients with colorectal carcinoma using a polyclonal thymidylate synthase antibody in comparison to the TS 106 monoclonal antibody. *J. Histochem. Cytochem.*, 48(6): 755-760.

Philippova T. M.; Novoselov, V. I.; Alekseev, S. I. 1994. Influence of microwaves on different types of receptors and the role of peroxidation of lipids on receptor-protein shedding. *Bioelectromagnetics*, 15 (3): 183-192.

Roy, I.; Gupta, M. N. 2003. Applications of microwaves in biological sciences. *Current Science*, 85(12): 1685-1693.

Bismuto, E.; Mancinelli, F; d'Ambrosio, G.; Massa, R. 2003. Are the conformational dynamics and the ligand binding properties of myoglobin affected by exposure to microwave radiation? *Eur. Biophy. J.*, 32(7): 628-634.

Porcelli, M.; Cacciapuoti, G.; Fusco, S.; Massa, R.; d'Ambrosio, G.; Bertoldo, C.; DeRosa, M.; Zappia V. 1997. Non-thermal effects of

(56) References Cited

OTHER PUBLICATIONS microwaves on proteins: Thermophilic enzymes as model system. *FEBS Letters*, 402 (2-3): 102-106.
Adam, D. 2003. Microwave chemistry: Out of the kitchen. *Nature*, 421(6923): 571-572.
Whittaker, A. G.; Mingos, D. M. P. 1995. Microwave-assisted solid-state reactions involving metal powders. *J. Chem. Soc. Dalton Trans.*, 12: 2073-2079.
Kappe, C. O. 2002. High-speed combinatorial synthesis utilizing microwave irradiation. *Curr. Opin. Chem. Biol.*, 6(3): 314-320.
Whittaker, A.G., and Mingos, D.M.P. 1993. Microwave-assisted solid-state reactions involving metal powders and gases. *J. Chem. Soc. Dalton Trans*. 16:2541-2543.
Technology Vision 2020, The US Chemical Industry, Dec. 1996.
Micheva, K. D.; Holz, R. W.; Smith, S. J. 2001. Regulation of presynaptic phosphatidylinositol4,5-biphosphate by neuronal activity. *J. Cell Biol.*, 154(2): 355-368.
Link, S.; El-Sayed, M. A. 1999. Spectral properties and relaxation dynamics of surface plasmon electronic oscillations in gold and silver nanodots and nanorods. *J. Phys. Chem. B.*, 103(40): 8410-8426.
Kreibig, U.; Genzel, L. 1985. Optical-absorption of small metallic particles. *Surface Science*, 156: 678-700.
Gao, F.; Lu, Q.; Komarneni, S. 2005. Interface reaction for the self-assembly of silver nanocrystals under microwave-assisted solvothermal conditions. *Chem. Mater.*, 17(4): 856-860.
Liu, F-K.; Chang, Y-C.; Huang, P-W.; Ko, F-H.; Chu, T-C. 2004. Preparation of silver nanorods by rapid microwave heating. *Chem. Lett.*, 33(8): 1050-1051.
Liu, F-K.; Huang, P-W.; Chu, T-C.; Ko, F-H. 2005. Gold seed-assisted synthesis of silver nanomaterials under microwave heating. *Materials Letters*, 59 (8-9): 940-944.
Liu, F-K.; Huang, P-W.; Chang, Y-C.; Ko, C-J.; Ko, F-H.; Chu, T-C. 2005. Formation of silver nanorods by microwave heating in the presence of gold seeds. *J. Crystal Growth*, 273 (3-4): 439-445.
Liu, F-K.; Huang, P-W.; Chang, Y-C.; Ko, F-H.; Chu, T-C. 2004. Microwave-assisted synthesis of silver nanorods. *J. Mater. Res.*, 19 (2): 469-473.
Aslan, K..; Lakowicz, J. R.; Geddes, C.D. 2004. Nanogold-plasmon-resonance-based glucose sensing. *Anal. Biochem.*, 330(1): 145-155.
Green, N. M. 1975. Avidin. *Adv. Protein Chem.*, 29: 85-133.
Wilchek, M.; Bayer, E. A. 1988. The avidin-biotin complex in bioanalytical applications. *Anal. Biochem.*, 171, 1-6.
Sokolov, K.; Chumanov, G.; Cotton, T. M Enhancement of molecular fluorescence near the surface of colloidal metal films. *Anal. Chem*. 1998, 70, 3898-3905.
Chicoine, L., and Webster, P. 1998. Effect of microwave irradiation on antibody labeling efficiency when applied to ultrathin cryosections through fixed biological material. Micro Res. Tech. 42(1):24-32.
Rangell, L. K., and Keller, G. A. 2000. Application of microwave technology to the processing and immunolabeling of plastic-embedded and cryosections. J. Histochem. Cytochem. 48(8):1153-1160.
Schichnes, D., Nemson, J., Sohlberg, L., and Ruzin, S. E. 1999. Microwave protocols for paraffin microtechnique and in situ localization in plants. Micro Microanalysis 4(5):491-496.

Rassner, U. A., Crumrine, O. A., Nau, P., and Elias, P. M. 1997. Microwave incubation improves lipolytic enzyme preservation for ultrastructural cytochemistry. Histochem. J. 29(5): 387-392.
Rivas L., Sanchez-Cortes S., Garcia-Ramos J. V. and Morcillo G. (2001). Growth of silver colloidal particles obtained by citrate reduction to increase the Ramen enhancement factor. *Langmuir*, 17(3) 574-577.
Pastoriza-Santos I. and Liz-Marzan L. M. (2000). Reduction of silver nanoparticles in DMF. Formation of monolayers and stable colloids. *Pure Appl. Chem.*, 72(1-2) 83-90.
Pastoriza-Santos I., Serra-Rodriquez C. and Liz-Marzan L. M. (2000). Self-assembly of silver particle monolayers on glass from $Ag^+$ solutions in DMF. *J. Colloid Interface Sci.*, 221(2) 236-241.
Bright R., Musick M. D. and Natan M. J. (1998). Preparation and characterization of Ag colloid monolayers. *Langmuir*, 14(20) 5695-5701.
Ni F. and Cotton T. M. (1986). Chemical procedure for preparing surface-enhanced Raman scattering active silver films. *Anal. Chem.*, 58(14) 3159-5163.
Freeman R. G., Grabar K. C., Allison K. J., Bright R. M., Davis J. A., Guthrie A. P., Hommer M. B., Jackson M. A., Smith P. C., Walter D. G. and Natan M. J. 1995. Self-assembled metal colloid monolayers—an approach to SERS substrates. *Science*, 267(5204): 1629-1632.
Grabar K. C., Freeman R. G., Hommer M. B. and Natan M. J. 1995. Preparation and characterization of Au colloid monolayers. *Anal. Chem.*, 67(4): 735-743.
Akins, R.E.; Tuan, R, S. 1995. Ultrafast protein determinations using microwave enhancement. *Mol. Biotechnol.*, 4(1): 17-24.
Kreibig U., Gartz M. and Hilger A. 1997. Mie resonances: Sensors for physical and chemical cluster interface properties. *Ber. Bunsenges, Phys. Chem.*, 101(11): 1593-1604.
Schray, C. L., Metz, A. L., and Gough, A. W. 2002. Microwave-enhanced fixation for rapid preparation of tissue sections for microscopic evaluation. Histologic. 35(1):7-12.
Vo-Dinh, T., Sepaniak, M. J., Griffin, G. D., and Alarie, J. P. 1993. Immunosensors: Principles and Applications. *Immunomethods*, 3:85-92.
Croppo, G. P.; Visvesvara, G. S.; Leitch, G.J.; Wallace, S.; Schwartz, D. A. 1998. Identification of the microsporidian Encephalitozoon hellem using immunoglobulin G monoclonal antibodies. *Archives of Pathology and Laboratory Medicine*, 122(2): 182-186.
Sridar V. 1997. Rate acceleration of Fischer-indole cyclization by microwave irradiation. *Indian ournal of Chemistry Section B-Organic Chemistry Including Medicinal Chemistry*, 36(1): 86-87.
DiCesare, N., Lakowicz, J.R. 2001. Wavelength-ratiometric probes for saccharides based on donor-acceptor diphenylpolyenes. *J. Photochemistry & Photobiology A: Chem*, 143: 39-47.
Lukomska, Joanna et al. "Two-photon induced fluorescence of Cy-5DNA in buffer solution and on silver island films." Biochemical and Biophysical Research Communications 328 (2005) 78-84.
Milton, Heather L. et al. "Synthesis and coordination of 2-diphenylphosphinothio-phenocarboxamide and bis(2,5-diphenylphosphinepicolinamide)." Polyhedron 23 (2004) 2575-2585.

* cited by examiner

MICROWAVE ACCELERATED ASSAYS

CROSS-REFERENCE TO RELATED APPLICATIONS

This application is a continuation application of claims priority to U.S. patent application Ser. No. 13/267,221, filed on Oct. 6, 2011, now U.S. Pat. No. 8,318,087, which in turn was a divisional application of U.S. patent application Ser. No. 11/719,731, now U.S. Pat. No. 8,034,633, which claimed priority of International Patent Application No. PCT/US2005/042050 on filed on Nov. 21, 2005, which in turn claimed priority of U.S. Provisional Application No. 60/629,822 filed on Nov. 19, 2004; U.S. Provisional Application No. 60/640,290 filed on Dec. 30, 2004 and U.S. Provisional Application No. 60/707,083 filed on Aug. 10, 2005.

GOVERNMENT RIGHTS IN INVENTION

Work related to the invention was conducted in the performance of a grant from the National Institute of General Medical Sciences GM070929 and National Center for Research Resources RR-08119. As a result of such contracts, the U.S. Government has certain rights in the invention described herein.

BACKGROUND OF THE INVENTION

1. Technical Field

The present invention is directed to a detection system and method for increasing sensitivity and rapidity of the detection system, and more particularly, to increasing fluorescence detection in surface assay systems while increasing kinetics of a bioreaction in the detection system.

2. Background of Related Art

Immunoassays are used widely for the detection and determination of a variety of proteins, peptides and small molecules.[1-8] While there exists a large diverse family of immunoassays today, the basic principles are mostly the same.[1-8] These typically use antigen-antibody binding for analyte recognition and mostly fluorescence based readout for signal transduction. Fluorescent based immunoassays are available in many forms, such as time-resolved immunoassays,[9-13] energy transfer immunoassays[14-16] and fluorescence polarization immunoassays.[17,18] The antigen-antibody recognition step is most often kinetically very slow, requiring long incubation times, very few assays subsequently being complete less than 10 minutes.[1-8] In addition, the sensitivity of fluorescence based immunoassays is mostly governed by the quantum yield of the tagging fluorophore and the efficiency and sensitivity of the detection system.[1-8] These two physical constraints underpin both the rapidity and sensitivity of current immunoassays.[1-8]

The present inventor, along with his colleagues, discovered that close-proximity to metallic silver islands or colloids can alter the radioactive decay rate and/or excitation rate of fluorophores. Further, it has been shown that quantum yield of low quantum yield fluorophores can be increased by proximity to metallic surfaces. The enhanced excitation of fluorophores in close proximity to metallic surfaces including nanostructures, islands, colloids, porous and continuous surfaces can have numerous applications in the biochemical and biological applications of fluorescence because of the increased intensity of the fluorescence.

Fluorescence detection is the basis of most assays used in drug discovery and high throughput screening (HTS) today. In all of these assays, assay rapidity and sensitivity is a primary concern. The sensitivity is determined by both the quantum yield of the fluorophores and efficiency of the detection system, while rapidity is determined by the physical and biophysical parameters of temperature, concentration, assay bioaffinity etc.

However, the assays and system discussed hereinabove, are limited by the reaction time of the chemical reactions within the assays, such as that which occur in binding or hybridization. Thus, there is a need for assay systems and methods that increase the biological/biochemical kinetics of the reaction, increase the sensitivity and that can be used for in both clinical and emergency room assessments.

SUMMARY OF THE INVENTION

In one aspect the present invention relates to an assay detection method comprising:
providing a conductive metallic material; wherein the metallic material is shaped as a film, particles, nanostructures, island or colloids;
introducing at least one biomolecule for disposing near the conductive metallic material, wherein the biomolecule is capable of emitting light and enhanced by a predetermined proximity to the metallic material;
applying electromagnetic energy in the microwave range to cause an increase in heat in the metallic material thereby increasing the kinetics of chemical reactions involving the biomolecule; and
measuring the emitted light from the system.

The method described above may be used in multiple fluorescence detecting systems, including but not limited to, Microwave Accelerated Metal-Enhanced Fluorescence (MA-MEF) and Microwave Accelerated Surface Enhanced Raman Scattering (MASERS). Further, the use of low power microwaves may be used in many different assays, including but not limited to, immunoassays, hybridization assays, resonance energy transfer assays, polarization/anisotropy based assays, chemiluminescence based assays, luminescence based assays, enzyme-linked immunosorbent assays.

In another aspect, the present invention provides for a detection system comprising:
a. a conductive metallic material positioned within a container, wherein the metallic material is shaped as a film, particles, nanostructures, island or colloids;
b. at least one biomolecule for disposing near the conductive metallic material, wherein the biomolecule is capable of emitting light and enhanced by a predetermined proximity to the metallic material;
c. an electromagnetic energy source that emits energy in at least the microwave range to cause an increase in heat in the metallic material thereby increasing the kinetics of a chemical reactions involving the biomolecule; and
d. a measuring device to measure the emitted light from the system.

In the present embodiment, the biomolecule comprises a fluorescing component that has the ability to fluoresce when contacted with radiation in the range from UV or IR. Preferably, the fluorescing component is a molecule that does not interfere with the chemical reaction of the biomolecule.

In another aspect the present invention relates to a method of metal-enhanced fluorescence sensing, comprising:
a. applying a conductive metallic material to a surface used in a detection system, wherein the surface includes glass, quartz, or a polymeric material;
b. introducing a solution containing at least one biomolecule for disposing near the conductive metallic surface, wherein the biomolecule is capable of fluorescing;

c. applying electromagnetic energy in the microwave range to cause an increase in heat in the solution thereby increasing the kinetics of any chemical reactions occurring within the detection system;

d. exciting the biomolecule with an electromagnetic source to cause fluorescing; and e. measuring the fluorescence emission within the system.

In yet another aspect, the present invention provides a method for detecting a targeted pathogen in a sample, the method comprising:

a. providing a system comprising:
  i. an immobilized metallic material positioned on a surface substrate, wherein the immobilized metallic material has attached thereto an immobilized capture DNA sequence probe complementary to a known DNA sequence of the target pathogen; and
  ii. a free capture DNA sequence probe complementary to a known DNA sequence of the target pathogen, wherein the free capture DNA sequence probe has attached thereto a fluorophore;

b. contacting the sample with the immobilized capture DNA sequence probe, wherein the DNA sequence of the target pathogen binds to the immobilized capture DNA sequence probe;

c. contacting the bound DNA sequence of the target pathogen with the free capture DNA sequence probe, wherein binding of the free capture DNA sequence probe to the DNA sequence of the target pathogen causes the fluorophore to be positioned a sufficient distance from the immobilized metallic material to enhance fluorescence emission;

d. irradiating the system with microwave energy in an amount sufficient to enhance binding of the free capture DNA sequence probe to the DNA sequence of the target pathogen causing increased speed of the reactions; and e. irradiating the system with electromagnetic energy in a range from UV to IR to increase fluorescence emission by the fluorophore positioned a predetermined distance from the metallic material.

Preferably, the microwave energy is sufficient to transfer energy to the metallic material thereby causing an increase of heat therein.

Preferably, the conductive metallic material takes the form of metallic particles, nanostructures, islands, colloids, porous matrix or a continuous metallic surface. The metallic element may include any form of noble metals such as silver, gold, platinum and copper, and more preferably the metallic material is silver, such as a low-density silver.

The biomolecule that is capable of fluorescing and/or upon excitation by electromagnetic energy emits light includes, but is not limited to fluorophores, chromophores, or lumophores. The compound capable of fluorescing may be an intrinsic fluorophore or a compound attached to an extrinsic fluorophore.

In a still further aspect, the present invention relates to an assay using High Throughput Screening (HTS), the method comprising:

a. providing a well plate used in HTS systems comprising a multiplicity of wells;

b. introducing metallic nanostructures into the wells, c. introducing at least one biomolecule for disposing near the metallic nanostructures, wherein the biomolecule is capable of emitting light and enhanced by a predetermined proximity to the metallic nanostructures;

d. applying electromagnetic energy in the microwave range to cause an increase in heat in the metallic material thereby increasing the kinetics of a chemical reactions involving the biomolecule; and e. measuring the emitted light from the system.

A further aspect of the present invention, relates to a kit for detecting a target molecule in a sample, the kit comprising a. a container comprising a layer of immobilized metal particles deposited on a substrate fabricated of a polymeric or quartz material, wherein an immobilized probe is connected to the metal particles and wherein the immobilized probe has an affinity for the target molecule;

b. a fluorophore having an affinity for the target molecule, wherein the binding of the target molecule to both the immobilized probe and fluorophore causes the fluorophore to be positioned a sufficient distance from the immobilized metal particles to enhance fluorescence emission; and c. a source of microwave energy.

Other aspects and advantages of the invention will be more fully apparent from the ensuing disclosure and appended claims.

DETAILED DESCRIPTION OF THE INVENTION

Figure 1:
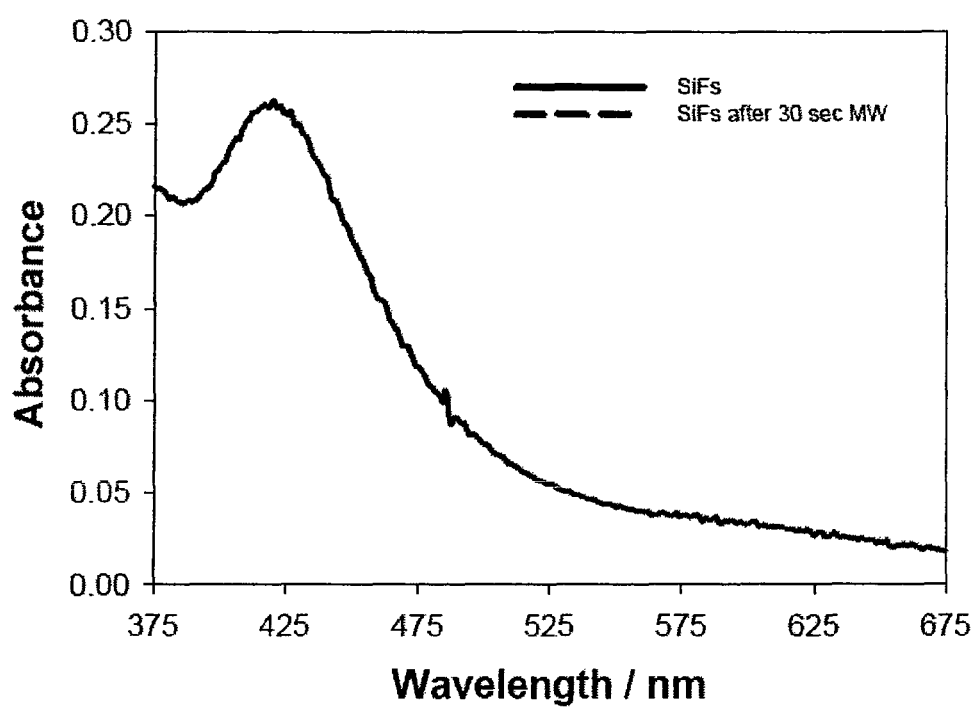
FIG. 1 shows the Silver island film (SiFs) plasmon absorption spectrum before and after exposure to low power microwaves.

The present invention relates to systems and methods for increasing and detecting the fluorescence of fluorescent and non-fluorescent compounds, including biomolecules, while increasing the kinetics of bioreactions used in detection methods.

"Fluorophore," as used herein, means any substance that emits electromagnetic energy such as light at a certain wavelength (emission wavelength) when the substance is illuminated by radiation of a different wavelength (excitation wavelength) and is intended to encompass a chemical or biochemical molecule or fragments thereof that is capable of interacting or reacting specifically with an analyte of interest in a sample to provide one or more optical signals. Additionally fluorophore includes both extrinsic and intrinsic fluorophores. Extrinsic fluorophore refer to fluorophores bound to another substance. Intrinsic fluorophores refer to substances that are fluorophores themselves. Exemplary fluorophores include but are not limited to those listed in the Molecular Probes Catalogue which is incorporated by reference herein.

Representative fluorophores include but are not limited to Alexa Fluor® 350, Dansyl Chloride (DNS-Cl), 5-(iodoacetamida)fluoroscein (5-IAF); fluoroscein 5-isothiocyanate (FITC), tetramethylrhodamine 5-(and 6-)isothiocyanate (TRITC), 6-acryloyl-2-dimethylaminonaphthalene (acrylodan), 7-nitrobenzo-2-oxa-1,3,-diazol-4-yl chloride (NBD-Cl), ethidium bromide, Lucifer Yellow, 5-carboxyrhodamine 6G hydrochloride, Lissamine rhodamine B sulfonyl chloride, Texas Red™. sulfonyl chloride, BODIPY™., naphthalamine sulfonic acids including but not limited to 1-anilinonaphthalene-8-sulfonic acid (ANS) and 6-(p-toluidinyl)naphthalene-2-sulfonic acid (TNS), Anthroyl fatty acid, DPH, Parinaric acid, TMA-DPH, Fluorenyl fatty acid, Fluorescein-phosphatidylethanolamine, Texas red-phosphatidylethanolamine, Pyrenyl-phophatidylcholine, Fluorenyl-phosphotidylcholine, Merocyanine 540, 1-(3-sulfonatopropyl)-4-[-.beta.-[2[(di-n-butylamino)-6 naphthyl]vinyl]pyridinium betaine (Naphtyl Styryl), 3,3' dipropylthiadicarbocyanine (diS-$C_3$-(5)), 4-(p-dipentyl aminostyryl)-1-methylpyridinium (di-5-ASP), Cy-3 Iodo Acetamide, Cy-5-N-Hydroxysuccinimide, Cy-7-Isothiocyanate, rhodamine 800, IR-125, Thiazole Orange, Azure B, Nile Blue, Al Phthalocyanine, Oxaxine 1,4',6-diamidino-2-phenylindole (DAPI), Hoechst 33342, TOTO, Acridine Orange, Ethidium Homodimer, N(ethoxycarbonylmethyl)-6-methoxyquinolinium (MQAE), Fura-2, Calcium Green, Carboxy SNARF-6, BAPTA, coumarin, phytofluors, Coronene, and metal-ligand complexes.

Representative intrinsic fluorophores include but are not limited to organic compounds having aromatic ring structures including but not limited to NADH, FAD, tyrosine, tryptophan, purines, pyrirmidines, lipids, fatty acids, nucleic acids, nucleotides, nucleosides, amino acids, proteins, peptides, DNA, RNA, sugars, and vitamins. Additional suitable fluorophores include enzyme-cofactors; lanthanide, green fluorescent protein, yellow fluorescent protein, red fluorescent protein, or mutants and derivates thereof.

Also included are novel quaternary nitrogen heterocyclic boronic acid-containing compounds including:

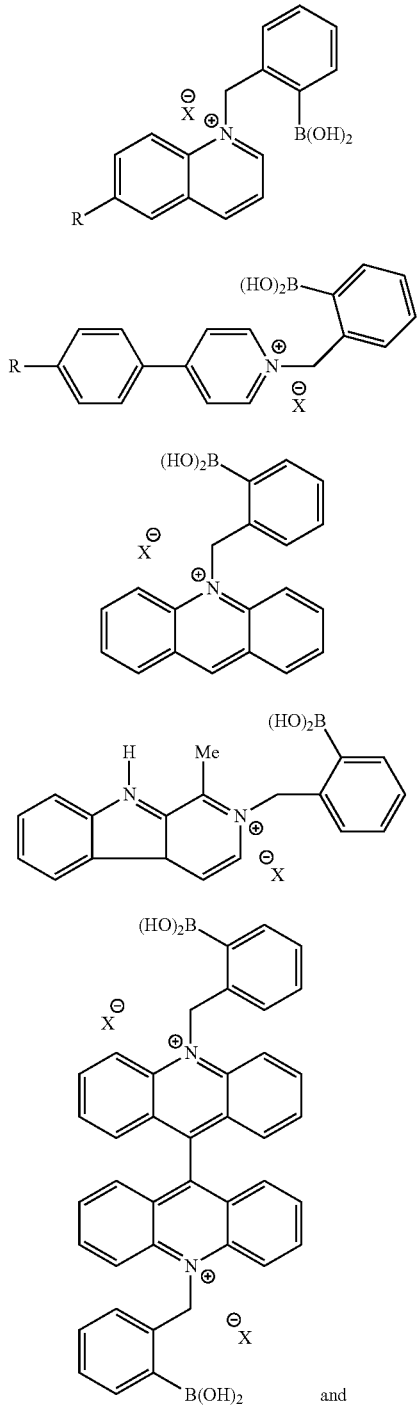

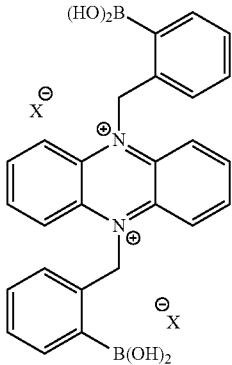

wherein X is chloride, bromide or iodide and R is selected from the group consisting of H, straight chain or branched $C_1$-$C_4$ alkyl group, $C_1$-$C_4$ alkoxy group, aryl group, hydroxyl, cyano, sulfonyl, and $NR^1R^2$, wherein $R^1$ and $R^2$ may be the same as or different from one another and is independently selected from the group consisting of H and $C_1$-$C_4$ alkyl groups.

The term "biomolecule" means any molecule occurring in nature or a derivative of such a molecule. The biomolecule can be in active or inactive form. "Active form" means the biomolecule is in a form that can perform a biological function. "Inactive form" means the biomolecule must be processed either naturally or synthetically before the biomolecule can perform a biological function. Exemplary biomolecules include nucleic acids, aromatic carbon ring structures, NADH, FAD, amino acids, carbohydrates, steroids, flavins, proteins, DNA, RNA, oligonucleotides, peptide, nucleic acids, fatty acids, myoglobin, sugar groups such as glucose etc., vitamins, cofactors, purines, pyrimidines, formycin, lipids, phytochrome, phytofluor, peptides, lipids, antibodies and phycobiliproptein.

The invention combines the use of metal-enhanced fluorescence with the ability to greatly speed up biological/biochemical kinetics by using low level microwave heating of the samples. Low level microwaves do not destroy or denature proteins, DNA, or RNA, but instead heat the sample sufficiently to provide for accelerated kinetics such as binding or hybridization. In addition, the microwaves are not scattered by the low density silver metal, which is contrary to most metal objects such as that recognized by placing a spoon in a microwave oven. Hence, the present invention combines the enhanced and localized signal intensities that have been reported for metals in close proximity to fluorophores with the ability to rapidly heat the samples using low level microwaves.

Microwaves (about 0.3 to about 300 GHz) lie between the infrared and radiofrequency electromagnetic radiations. It is widely thought that microwaves accelerate chemical and biochemical reactions by the heating effect,[55] where the heating essentially follows the principle of microwave dielectric loss.[42] Polar molecules absorb microwave radiation through dipole rotations and hence are heated, where as non-polar molecules do not absorb due to lower dielectric constants are thus not heated.[42] The polar molecules align themselves with the external applied field. In the conventional microwave oven cavity employed in this work, the radiation frequency (2450 MHz) changes sign $2.45 \times 10^9$ times per second. Heating occurs due to the tortional effect as the polar molecules rotate back and forth, continually realigning with the changing field, the molecular rotations being slower than the changing electric field. The dielectric constant, the ability of a molecule to be polarized by an electric field, indicates the capacity of the medium to be microwave heated. Thus, solvents such as water, methanol and dimethyl formamide are easily heated, where as microwaves are effectively transparent to hexane, toluene and diethylether.[42] For metals, the attenuation of microwave radiation arises from the creation of currents resulting from charge carriers being displaced by the electric field.[58] These conductance electrons are extremely mobile and unlike water molecules can be completely polarized in 10-18 s. In microwave cavity used in the present invention, the time required for the applied electric field to be reversed is far longer than this, in fact many orders of magnitude. If the metal particles are large, or form continuous strips, then large potential differences can result, which can produce dramatic discharges if they are large enough to break down the electric resistance of the medium separating the large metal particles. Interestingly, and most appropriate for the new assay platform described herein, small metal particles do not generate sufficiently large potential differences for this "arcing" phenomenon to occur.[58] However, as discuss hereinbelow, the charge carriers which are displaced by the electric field are subject to resistance in the medium in which they travel due to collisions with the lattice phonons.[58] This leads to Ohmic heating of the metal nanoparticles in addition to the heating of any surface polar molecules. Intuitively, this leads to localized heating around the silver nanostructures in addition to the solvent, rapidly accelerating assay kinetics. Further, the close proximity of assay fluorophores, additionally leads to fluorophore radiative decay rate modifications[22,37] and the subsequent increase in fluorescence emission.[22,37] Hence metallic nanoparticles, fluorophores and microwaves can be combined to yield kinetically accelerated and optically amplified immunoassays.

There are many important assays that can directly benefit from enhanced signal intensities and quicker kinetics. For example, myoglobin concentrations for heart attack patients, patients of toxic shock and pancreatitus. All of these assays are widely used in hospitals emergency rooms with assay times of greater than 30 minutes. Thus, the present invention can be used for points-of-care clinical assessment in emergency rooms.

In the present invention, microwave radiation is provided by an electromagnetic source having a frequency in a range between 0.3 and 10 GHz and a power level in a range between about 10 mwatts and 400 watts, more preferably from 30 mwatts to about 200 watts. Any source, known to one skilled in the art may be used, such as a laser that emits light, wherein light is used in its broad sense, meaning electromagnetic radiation which propagates through space and includes not only visible light, but also infrared, ultraviolet and microwave radiation. Thus, a single instrument placed above the surface of the assay can be used to generate the microwave energy and energy to excite fluorescing molecules. The light can be emitted from a fiber continuously or intermittently, as desired, to maintain the metallic particles at a predetermined temperature such that it is capable of increasing the speed of chemical reactions within the assay system. In the alternative, microwave energy can be supplied through a hollow wave guide for conveying microwave energy from a suitable magnetron. The microwave energy is preferably adjusted to cause an increase of heat within the metallic material without causing damage to any biological materials in the assay system.

The present invention provides enhanced emissions using metallized islands of elliptical, spherical, triangular or rod-like forms. In exemplary cases, the elliptical islands have aspect ratios of 3/2, and the spherical colloids have diameters of 20-60 nm However, the invention is not limited to any particular geometry. Using known coating techniques, the placement of metallic islands could be controlled precisely, as close as 50 nm apart. In the continuous metallic film case, the fluorophore emissions could be detected in the analyte solution up to 500 nm away from the surface of the metal. In the case where the metallic coating is formed by islands, the enhanced fluorophore emissions could be detected in the solution up to 200 nm away from the surface of the metal.

In one embodiment the present invention provides for metallic material and a biomolecule capable of fluorescing, wherein the metallic material and the biomolecule are separated by at least one film spacer layer. The thickness of said film may be chosen so as to enhance the fluorescence of the biomolecule due to the distance of the biomolecule from the metallic material. The film spacer layer may be one or multiple layers of a polymer film, a layer formed from a fatty acid or a layer formed from an oxide. In a preferable embodiment, the film spacer layers and the metallic material are chemically inert and do not bind to the biomolecules to be detected or to intermediates that are bound to the compounds to be detected, for example covalently bound. The layer formed from a fatty acid may be formed by a Langmuir-Blodgett technique. The film spacer layer may be a spin coated polymer film. The oxide layer may be formed from a deposition technique, such as vapor deposition.

Further, the metallic material may be in the form of a porous three dimensional matrix. The three dimensional matrix may be a nano-porous three dimensional matrix. The metallic material may include metal colloid particles and/or metal-silica composite particles. The metallic material may comprise agglomerated metal particles and/or binary linked particles or metal particles in a polymer matrix. The three dimensional matrix may be formed from controlled pore glasses or using matrices assembled from the aggregation of silver-silica composites themselves. The matrices may be metallic nanoporous matrix, through which species will flow and be both detected and counted more efficiently.

Increase in Radiative Decay Rate

It is known that a nearby metal can increase the intrinsic decay rate of a fluorophore, that is, to modify the rate at which the fluorophore emits photons. In fluorescence, the spectral observables are governed by the magnitude of 2, the radiative rate, relative to the sum of the non-radiative decay rates, $k_{nr}$ such as internal conversion and quenching.

Fluorophores with high radiative rates have high quantum yields and short lifetimes. Increasing the quantum yield requires decreasing the non-radiative rates $k_{nr}$, which is often only accomplished when using a low solution temperature or a fluorophore bound in a more rigid environment. The natural lifetime of a fluorophore, $\tau_n$, is the inverse of the radiative decay rate or the lifetime which would be observed if their quantum yields were unity. This value is determined by the oscillator strength (extinction coefficient) of the electronic transition. Hence, for almost all examples currently employed in fluorescence spectroscopy, the radiative decay rate is essentially constant. The modification and control of the radiative rate have also been referred as Radiative Decay Engineering (RDE), or "lightening rod" fluorescence enhancement effect. For example, enhanced intrinsic DNA fluorescence above metallic particles has recently been observed, which is typically not readily observable because of DNA's very low quantum yield of less than $10^{-4}$. The second favorable "lightening rod" effect also increases the fluorescence intensity by locally enhanced excitation. In this case, emission of fluorophores can be substantially enhanced irrespective of their quantum yields.

The reduction in lifetime of a fluorophore near a metal is due to an interaction between the fluorophore and metal particle, which enhances the radiative decay rate (quantum yield increase) or depending on distance, $d^{-3}$, causes quenching. It should be noted that lifetimes of fluorophores with high quantum yields (0.5) would decrease substantially more than the lifetimes of those with low quantum yields (0.1 and 0.01). A shorter excited-state lifetime also allows less photochemical reactions, which subsequently results in an increased fluorophore photostability. Notably, the use of low quantum yield fluorophores would lead to much larger fluorescence enhancements (i.e. $1/Q_O$) and could significantly reduce unwanted background emission from fluorophores distal from the silvered assay.

Fluorophore photostability is a primary concern in many applications of fluorescence. This is particularly true in single molecule spectroscopy. A shorter lifetime also allows for a larger photon flux. The maximum number of photons that are emitted each second by a fluorophore is roughly limited by the lifetime of its excited state. For example, a 10 ns lifetime can yield about $10^8$ photons per second per molecule, but in practice, only $10^3$ photons can be readily observed. The small number of observed photons is typically due to both photodestruction and isotropic emission. If a metal surface decreases the lifetime, one can obtain more photons per second per molecule by appropriately increasing the incident intensity.

On the other hand, the metal-enhanced fluorescence provides enhanced intensity, while simultaneously shortening the lifetime. That is, it may be possible to decrease the excitation intensity, yet still see a significant increase in the emission intensity and photostability.

The ability to increase the radiative decay rate suggests that any chromophore, even non-fluorescent species such as bilirubin, fullerenes, metal-ligand complexes or porphyrins could display usefully high quantum yields when appropriately placed near a metal surface. The effects of metal surface-fluorophore interactions are highly dependent upon the distance between the metal surface and the species, and the nature of the metal surface.

The emission enhancement may be observed at distances according to the type of fluorophore to be detected and the type of metal. For example, emission enhancement may be observed when a fluorophore distances about 4 nm to about 200 nm to metal surfaces. Preferable distances are about 4 nm to about 30 nm, and more preferably, 4 nm to about 20 nm to metal surfaces. At this scale, there are few phenomena that provide opportunities for new levels of sensing, manipulation, and control. In addition, devices at this scale may lead to dramatically enhanced performance, sensitivity, and reliability with dramatically decreased size, weight, and therefore cost.

Different surface enhanced fluorescence effects are expected for mirrors, sub-wavelength or semi-transparent metal surfaces, silver island films or metal colloids. More dramatic effects are typically observed for islands and colloids as compared to continuous metallic surfaces. The silver islands had the remarkable effect of increasing the intensity 5-fold while decreasing the lifetime 100-fold. Such an effect can only be explained by an increase in the radiative decay rate, Fluorescence can be detected using devices including, but not limited to, a spectrofluorometer having a light source and detector. Light sources can include arc lamps and lasers. Detectors can include photomultiplier tubes. Additionally, it is advantageous for the device to have a monochromator so that specific wavelengths of light may be used to excite a molecule or to detect emissions at a specific wavelength. When a sample containing a fluorophore is placed in the spectrofluorometer and exposed to an amount of exciting radiation, the fluorophore emits radiation that is detected by a photomultiplier tube. The fluorescence intensity of a biomolecule can be increased in response to an amount of exciting radiation when the distance between the metal particle and the biomolecule is from about 40 Å to about 2000 Å, preferably from about 40 Å to about 200 Å. Alternatively, the fluorescence intensity of the biomolecule can be reduced when the distance between the biomolecule and the metal particle is less than about 40 Å.

The present invention provides a method for increasing the fluorescence intensity of a fluorescently labeled biomolecule including the steps of labeling a biomolecule with a fluorophore, positioning the labeled biomolecule at a distance apart from a metallic particle such that in response to an amount of exciting radiation in the microwave range, the fluorophore emits radiation.

In applications of MEF, it was found that the enhanced fluorescence signals (Quantum yields—Qm) of fluorophores in close proximity (<10 nm) to metallic nanostructures could be well described by the following equations:

$$Q_m = (\Gamma + \Gamma_m)/(\Gamma + \Gamma_m + k_{nr}) \quad (1)$$

where $\Gamma$ is the unmodified radiative decay rate, $\Gamma_m$ is the metal-modified radiative decay rate and $k_{nr}$ are the non-radiative rates. Similarly, the metal-modified lifetime, τm, of a fluorophore is decreased by an increased radiative decay rate:

$$\tau_m = 1/(\Gamma + \Gamma_m + k_{nr}) \quad (2)$$

These equations have resulted in most unusual predictions for fluorophore-metal combinations, and it is these predictions and observations that are currently finding profound implications and applications in fluorescence based nanotechnology.[19-22,37] Given that fluorescence has become the dominant tool in biotechnology today, then metal-enhanced[19-22,37] and plasmon coupled fluorescence[38,39] promises to change the way fluorescence is viewed.[40] From equations 1 and 2, it can be seen that as the value of Fm increases, the quantum yield Qm increases, while the lifetime, τm, decreases. This is contrary to most observations in fluorescence[40] where the free-space quantum yield, $Q_0$, and lifetime, $\tau_0$, usually change in unison as described by the well known equations:[40]

$$Q_0 = \Gamma/(\Gamma + k_{nr}) \quad (3)$$

$$\tau_0 = 1/(\Gamma + k_{nr}) \quad (4)$$

In addition, one major criterion for choosing fluorophores in current immunoassays has been a high quantum yield. This can lead to a high background from either unlabelled fluorophores or a high fluorescence background from non-specific assay absorption. However, metal-enhanced fluorescence is ideally suited in this regard, in that low quantum yield fluorophores are more favorable,[2,23,37] the fluorescence enhancement factor in the presence of silver nanostructures given by 1/Q0 where Q0 is the free-space[22] quantum yield in the absence of metal. Subsequently MEF when applied to immunoassays, yields ultra bright assays, with a much higher Signal:Noise as compared to identical assays not employing the MEF phenomenon.

Preparation of Metal Islands

The island particles are prepared in clean beakers by reduction of metal ions using various reducing agents.[83] For example, sodium hydroxide is added to a rapidly stirred silver nitrate solution forming a brown precipitate. Ammonium hydroxide is added to re-dissolve the precipitate. The solution is cooled and dried quartz slides are added to the beaker, followed by glucose. After stirring for 2 minutes, the mixture is warmed to 30° C. After 10-15 minutes, the mixture turns yellow-green and becomes cloudy. A thin film of silver particles has formed on the slides as can be seen from their brown green color. The slides are rinsed with pure water prior to use.

Alternative procedures for preparing metal particles are also available.[84,85,86,87,88] Silver is primarily used because of the familiar color from the longer surface plasmon absorption of silver.

Preparation of Silver Colloids

Colloids can be prepared as suspensions by citrate reduction metals. Preferred metals are silver and gold. Again, gold may be because of the absorption of gold at shorter wavelengths. However, gold colloids may be used with longer wavelength red and NIR fluorophores.

The size of the colloids and their homogeneity can be determined by the extensive publications on the optical properties of metal particles available and the effects of interface chemistry on the optical property of colloids.[89]

Silver island films can be formed by a chemical reduction of a silver salt on the quartz surface, which are relatively simple to fabricate. However, this approach does not provide a control of particle size, or distance of the fluorophores from the surface Enhancements of 1000 fold have been with the realization that sample geometries have been heterogeneous and the enhancement factors spatially averaged.

Metal particles can be bound to a surface by placing functional chemical groups such as cyanide (CN), amine ($NH_2$) or thiol (SH), on a glass or polymer substrate. Metal colloids are known to spontaneously bind to such surfaces with high affinity.[90,91,92]

Positioning of the biomolecule or metal particle at a desired distance can be achieved by using a film. The film may be a polymer film, a Langmuir-Blodgett film or an oxide film.

Langmuir-Blodgett Films

Metal-fluorophore distances may be achieved by using Langmuir-Blodgett films with fatty acid spacers. The fatty acids may be from natural sources, including concentrated cuts or fractionations, or synthetic alkyl carboxylic acids. Examples of the fatty acids include, but not limited to, caprylic ($C_8$), capric ($C_{10}$), lauric ($C_{12}$), myristic ($C_{14}$), palmitic ($C_{16}$), stearic ($C_{18}$), oleic ($C_{18}$), linoleic ($C_{18}$), linolenic ($C_{18}$), ricinoleic ($C_{18}$) arachidic ($C_{20}$), gadolic ($C_{20}$), behenic ($C22$) and erucic ($C_{22}$). The fatty acids with even numbered carbon chain lengths are given as illustrative though the odd numbered fatty acids can also be used.

Metal-fluorophore distances may be achieved by using polymer films. Examples of the polymer include, but not limited to, polyvinyl alcohol (PVA). Absorbance measurements and ellipsometry may be used to determine polymer film thickness. One type of polymer films is spin coated polymer film. The technology of spin coated polymer spacer films readily allows films to be coated onto a variety of surfaces, with varied thickness from >0.1 um. The coating can be performed on a spin coater, which allows uniform surface thickness by varying polymer concentration (viscosity) and spin speed. For example, Model P6700 spin coater (Specialty Coating Systems Inc.), allows uniform surface thickness by varying polymer concentration (viscosity) and spin speed.

In one embodiment, detection occurs without binding the molecules to the sensor or support. The molecule to be detected is not chemically bound. The molecule to be detected may remain in solution and not directly or indirectly interact with the metal particles, coatings or film spacer layers.

Metallic colloids (or various other non-spherical shapes/particles) may also be incorporated into organic polymers, covalently or non-covalently, to form polymeric matrices, wherein the distance from diffusing species affords an increase in radiative decay rate and thus, an increase in quantum yield. Such polymeric matrices are ideal for sensing/flowing sensing applications of low concentration species.

Polymers containing metal particles may have other applications, including but not limited to, size inclusion/exclusion sensing of non-fluorescent species, increased photostability of embedded fluorophores, single pore single molecule detection, and porous polymers which allow diffusing analytes or antibodies, resulting in a detectable and quantifiable signal change in the analyte or antibody or respective transduction element.

This embodiment of the present invention may also have vast applications in clinical medicine, environmental monitoring applications, homeland security such as rapid detection of low concentration species, industrial processes, pharmaceutical industries such as monitoring species, and sensors for use in reduced atmospheres such as biohazard clean rooms and space light.

The benefits of the present invention include an increase in fluorescence intensity due to increases in the excitation and radiative decay rates, and the present invention has many profound implications and applications in biochemical, biophysical, clinical testing and sensing. For example, that emission of low quantum yield chromophores can be increased has important implications for studies of nucleic acids and protein fluorescence. Likelihood that surface enhanced fluorescence can result in a million-fold more photons per fluorophore may provide an equivalent, if not surpassing PCR and ELISA in terms of sensitivity, for detection of infectious organisms without the need for the currently used amplification steps.

EXAMPLES

FIG. 1 shows the plasmon absorption spectra of Silver Island Films (SiFs), both before and after low power microwave heating for 30 seconds. The cavity power was approximately 140 watts, which is the same as utilized in the assays discussed later, and is of a similar power used for immunostaining[61,62] As can be seen from FIG. 1, the microwaves and heating had no effect on the surface plasmon absorption of the SiFs, indicating no structural or surface silver shape changes, where the surface plasmon absorption is well-known to be characteristic of the shape of the nanoparticles,[63,64] which is due to the mean free path oscillation of surface charges.[63,64] Further, no "sparking" was evident from the silvered surfaces, a known consequence of surface charge build-up and dissipation for large non-wavelength sized particles or continuous surfaces.[58]

Figure 2:
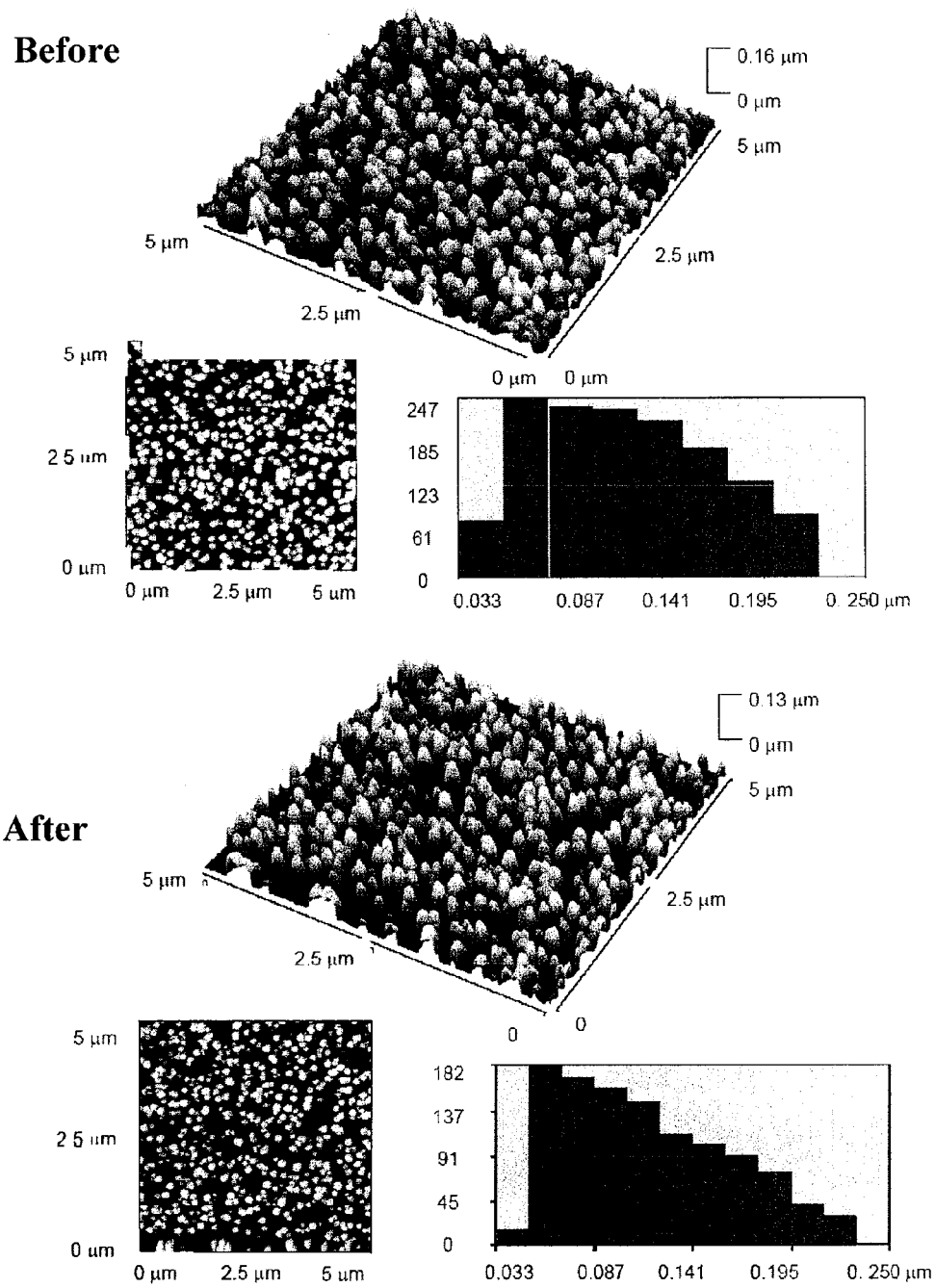
FIG. 2 shows the AFM images of silver Island films (SiFs) before and after 30 second exposure to low power microwaves.

The structural morphology of the silvered surfaces was additionally measured using Atomic Force Microscopy as shown in FIG. 2. While it is was somewhat difficult to probe that exact same area after microwave heating, very little, if no change in surface morphology was observed between the locations. While not shown in FIG. 2, the silvered surfaces, both wet and dry, was additionally exposed to several hundreds watts of microwave cavity power over many minutes. In all of these investigations no evidence for surface structural changes was found by microwave heating, clearly demonstrating the compatibility of the nanostructured surfaces to microwave exposure and therefore heating. In this regard, several solution based studies have recently reported the microwave induced growth of nanostructures, although these reports involved only the initial growth of the particles in the presence of stabilizing surfactants,[65-69] and not the exposure of finalized structures as described here.

Figure 3:
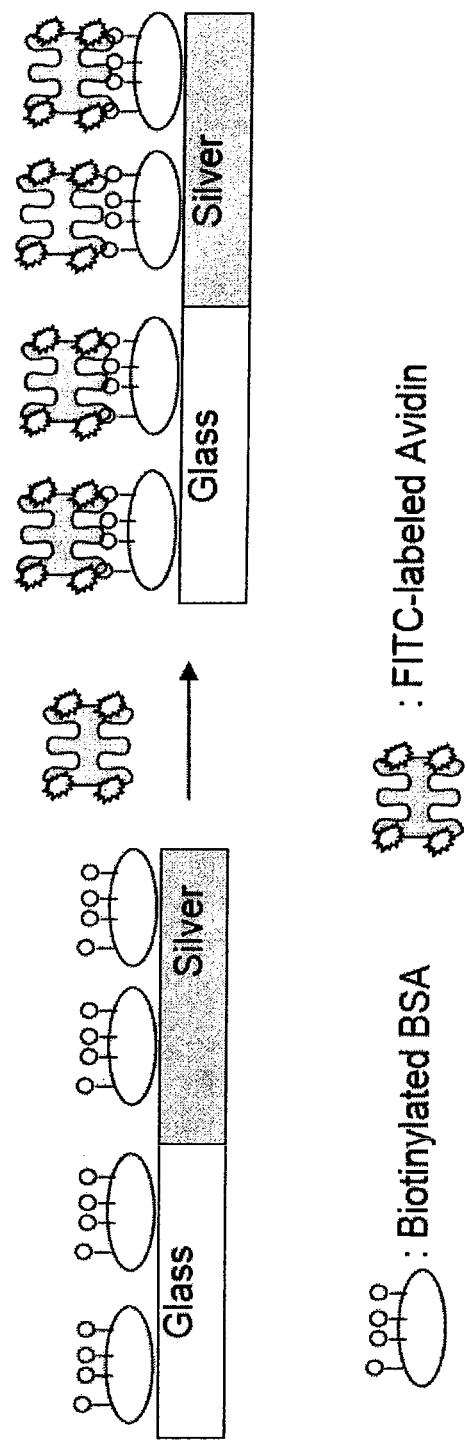
FIG. 3 shows the components of the model protein-fluorophore system used to demonstrate Microwave-Accelerated Metal-Enhanced Fluorescence (MAMEF). Both glass and silvered surfaces are equally coated with biotinylated-BSA which creates a spacer layer for metal-enhanced fluorescence. Fluorescein labeled avidin (FITC-Avidin) rapidly binds to the surface with a room temperature reaction time of about 30 minutes.

To demonstrate the utility of the herein described new platform assay approach, a model protein fluorophore system was chosen, FIG. 3, which equally coats one half of a silvered glass microscope slide, the other side non-silvered, acting as a control sample by which to compare the benefits of using the Metal-Enhanced Fluorescence (MEF) phenomenon. The enhancement ratio ISiFs/IGlass (the benefit of using the MEF phenomenon) is the fluorescence intensity observed on the SiFs divided by the Intensity on the non-silvered glass substrate. The biotinylated BSA readily forms a monolayer on both silver and glass substrates.[71-73] In addition, this protein system positions fluorophores >4 nm from the surfaces, which is ideal for MEF, which the present inventor has shown to be a through-space phenomenon,[22,23,37] as compared to Surface-Enhanced Raman Scattering SERS, a similar effect known to be due to surface contact interactions.[22] This model protein system also affords for simple kinetics, i.e. no back reactions are expected due to the well-known strong association of biotin and avidin.[71-73]

Figure 4:
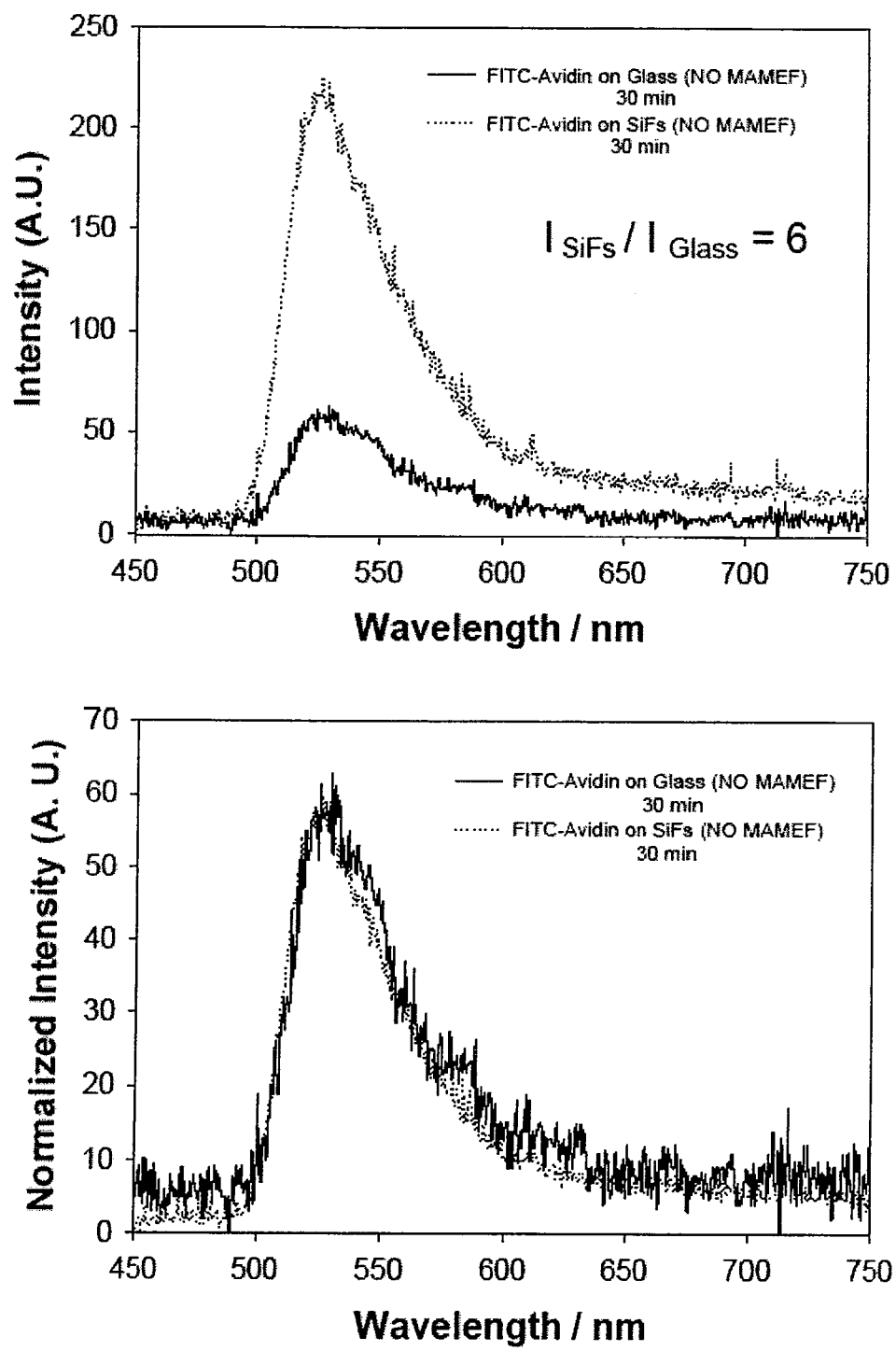
FIG. 4 shows the enhanced fluorescein emission from the silvered surface as compared to the glass surface (control sample) after 30 minutes incubation (Top). The samples were washed after incubation. (Bottom)—Normalized emission spectra showing that the emission spectral properties are preserved on both silvered and glass substrates.

FIG. 4—top shows the fluorescein emission intensity from both the silvered and glass (control sample) slide. The emission spectra, which is collected through a 500 nm long-pass filter, shows an approximate 6-fold greater intensity from the silver as compared to the glass control. This increase is due to a radiative rate modification of the fluorescein as it is brought into close proximity to the silver nanostructures by the bio-affinity reaction, and is consistent with numerous previous publications.[19-37] In FIG. 4—top the sample was incubated for 30 minutes at room temperature, which was predetermined to be sufficient enough time to allow the assay to go to >95% completion. FIG. 4—bottom shows the normalized spectra, demonstrating that the spectral properties are preserved on both the silver and glass substrates.

Figure 5:
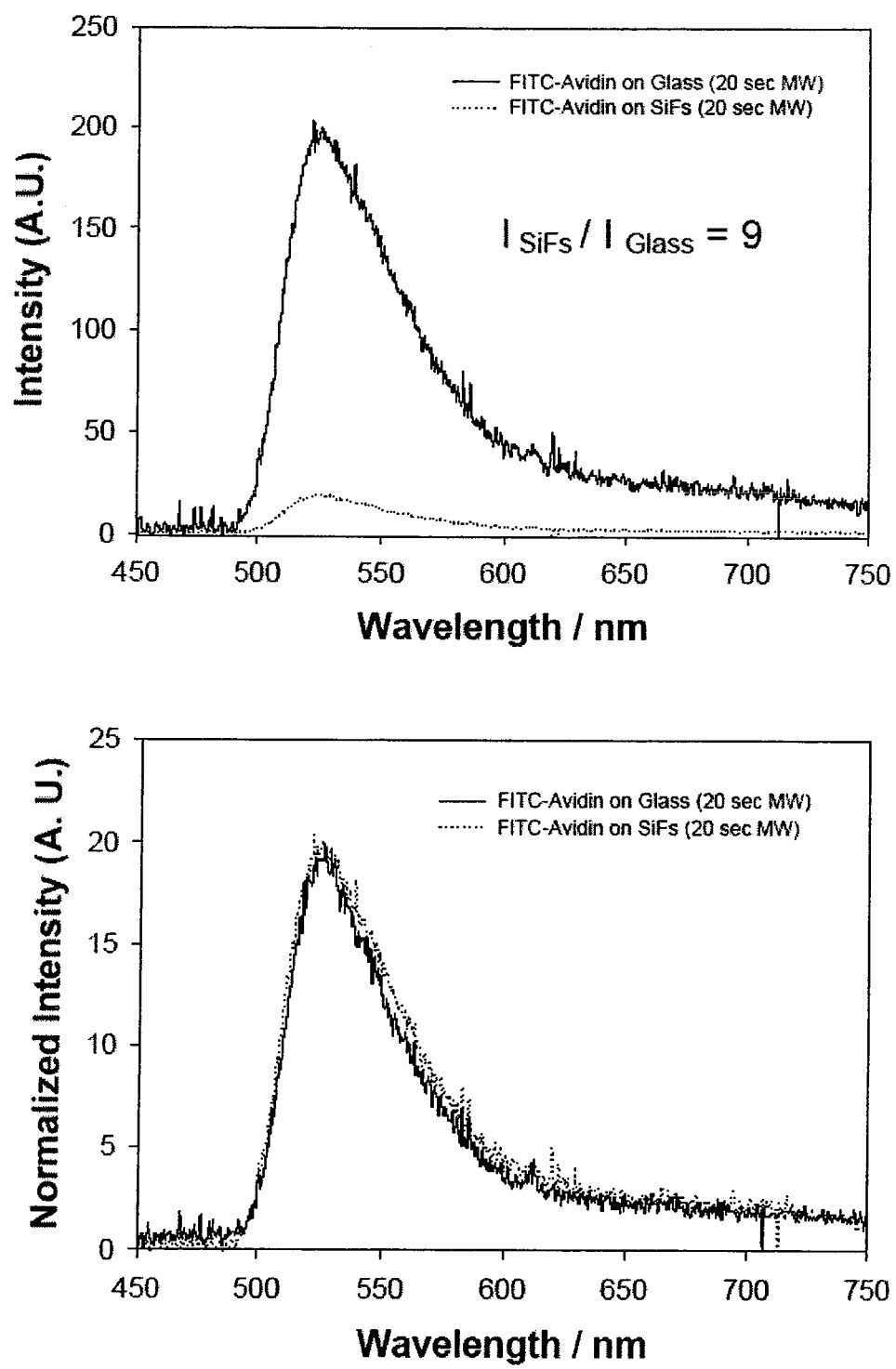
FIG. 5 shows the enhanced fluorescein emission on the silvered surface as compared to glass after 20 seconds low power microwave heating (top). The sample was washed after 20 seconds of microwaving to remove unbound material. A similar final fluorescein emission fluorescence Intensity can be seen for both a 30 minute incubation (FIG. 4—top) as compared to 20 seconds microwave heating. (Bottom)—Normalized emission spectra showing that the spectral properties are maintained.

FIG. 5—top shows the combined effect of both low power microwave heating and the optical amplification due to the silver[19-37] for an identical assay as measured in FIG. 4, i.e. MAMEF. Interestingly, the assay yields a similar final fluorescence intensity after 20 seconds microwave heating (about 200 au) as compared to a 30 minute room temperature incubation, c.f. FIGS. 4 and 5 top. In: Biotinylated BSA: FITC-labeled Avidin Silver Glass Silver addition, the silver still maintains its properties for optically enhancing the fluorescein emission, due to an intrinsic radiative rate modification.[22,23,37] FIG. 5—bottom shows that the properties of fluorescein are maintained when the spectra are normalized for comparison.

Figure 6:
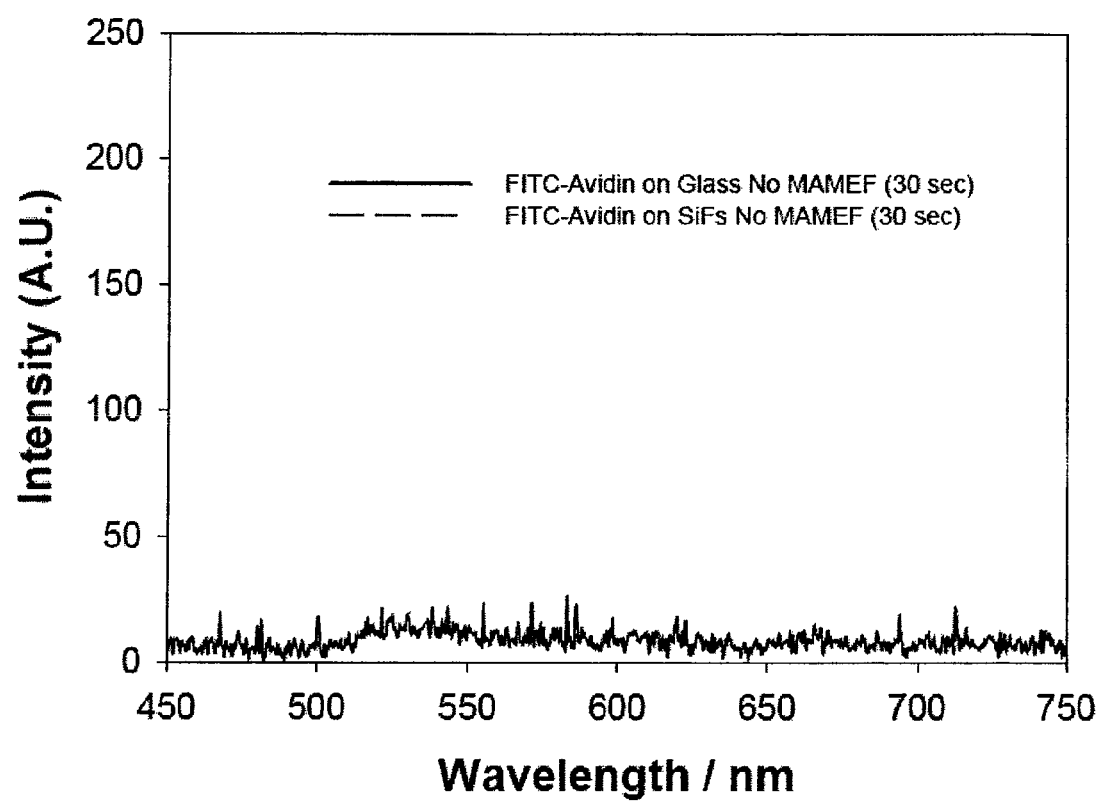
FIG. 6 shows the emission spectra of fluorescein-avidin on both silvered and glass surfaces after 30 seconds incubation, no microwave heating. The benefits of microwave accelerated metal-enhanced fluorescence can be seen by comparing FIGS. 4, 5 and 6.
Figure 7:
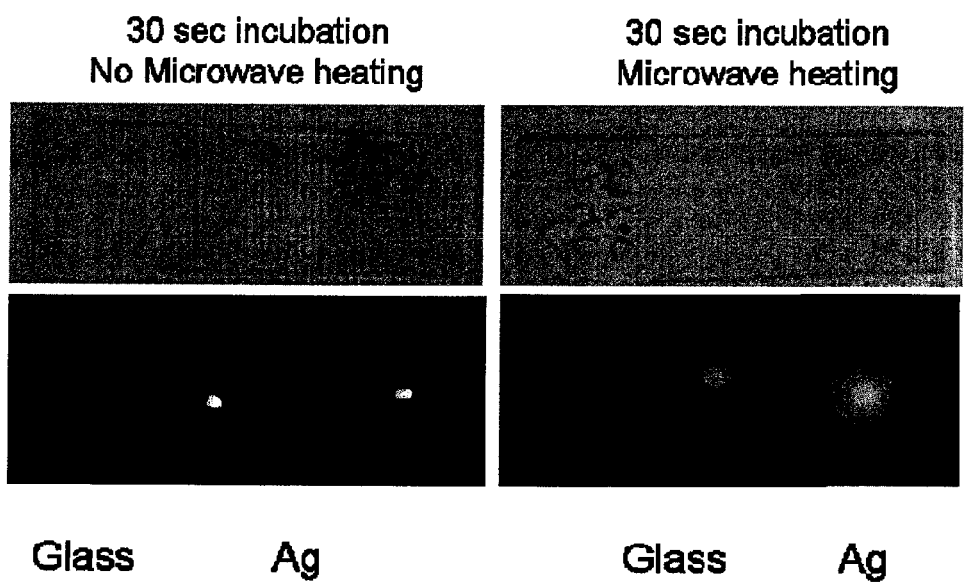
FIG. 7 shows photographs illustrating the benefits of Microwave-Accelerated Metal-Enhanced Fluorescence (MAMEF). Significantly, greater fluorescein fluorescence emission intensity can be seen on the silvered surface that has been microwave heated.

The assays were additionally incubated on both glass and silver for 30 seconds at room temperature, but with no microwave heating, as shown in FIG. 6. As can be seen, very little fluorescein labeled avidin was bound to the biotinylated-BSA surface, and when compared to the emission intensities shown in FIG. 5, then this clearly demonstrates the use of low power microwaves to increase the rapidity of the assay. This comparison is also evident visually in FIG. 7 wherein the photographs on the left taken through an emission filter after 30 seconds incubation and with no microwave heating, as compared to the right hand side photographs which show the much stronger fluorescence emission after 30 seconds microwave heating. The top photographs show the microscope slides, the silvered regions appearing brown in color and on the right-hand portion of each slide.

The benefits of microwave accelerated metal-enhanced fluorescence can be seen by comparing FIGS. 4, 5 and 6. Hence, FIGS. 5, 6 and 7 demonstrate the use of low power microwaves to rapidly heat samples and when combined with the use of silver nanostructures, readily affords for ultra bright and ultra fast assays. Interestingly, the microwaves do not perturb silver nanostructure morphology or even cause arcing, a familiar characteristic of metallic objects in microwave cavities.[58] Subsequently, this approach fundamentally addresses two underlying physical constraints of modern assays and immunoassays, namely assay sensitivity and rapidity. In this regard, the use of the SiFs provides for about a 10-fold increase in signal, which can be translated to increased 10-fold assay sensitivity, while the use of microwaves to facilitate mass protein transport to the surface provides for about a 90-fold decrease in assay run time.

A closer inspection and comparison of FIGS. 4 and 5 top, reveals that the rapidity of the assay is not equal on both the glass and silver substrates. After 30 minutes incubation (FIG. 4—top) the assay has a maximum emission intensity of about 60 au at 530 nm. In comparison, after 20 seconds microwave heating (FIG. 5—top), the emission intensity on the glass control has a value around 25 au. While this decrease lends itself to a larger enhancement ratio observed after microwave heating, i.e. 6 vs. 9, it is believed that this effect is due to the preferential local heating around the silver nanostructures,[58] rapidly accelerating mass transport to the surface. The temperature studies of the assays described herein, have shown that under the conditions employed, only an about 8° C. temperature jump occurred, which does not account for the 90-fold increase in assay rapidity, further supporting the notion of localized heating. Although it is likely that there may be contributions from additional plasma effects,[74] it is believed that the heating of metallic particles and powders by microwaves results primarily from conductive mechanisms.[58] Attenuation of the microwave radiation in a conductive medium arises from the creation of currents resulting from the charge carriers being displaced in the electric field. The charge carriers are subject to resistance, collisions with lattice phonons,[58] which lead to Ohmic heating.[58] In the present assay, this is thought to lead to the localized heating around the silver particles and is thought to explain the differences in assay rapidity on both the silver and glass substrates.

Figure 8:
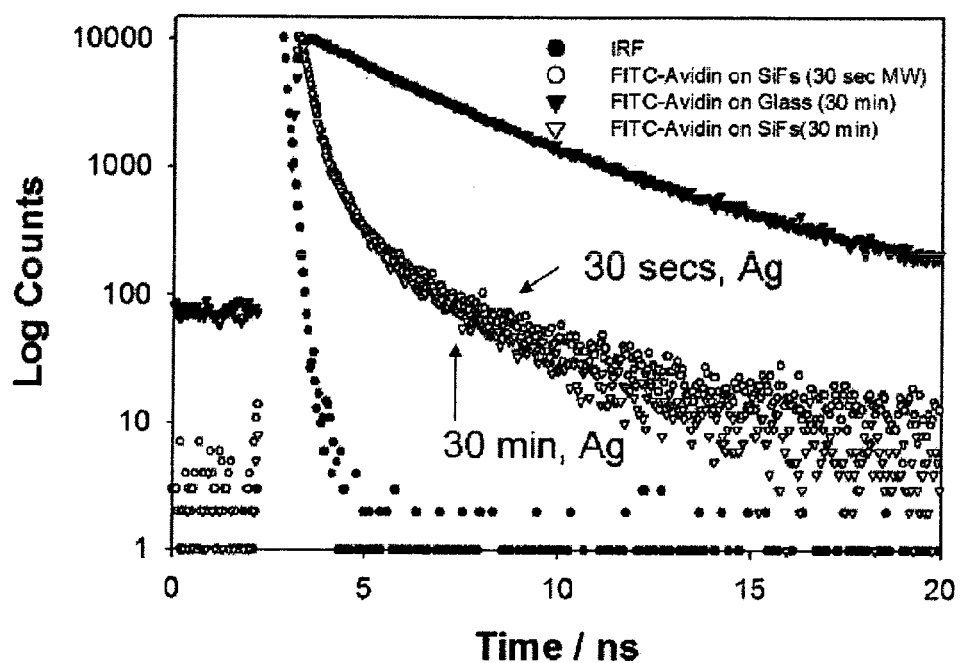
FIG. 8 shows intensity decays for FITC-Avidin on both glass and SiFs, both before and after exposure to low power microwave heating. The intensity decays on the SiFs are almost identical (SiFs—Silver Island Films).

As briefly described hereinabove, a fluorophore radiative decay rate modification can be characterized by an increased quantum yield (increased fluorescence intensity) coupled with a decreased lifetime, c.f. equations 1 and 2. The fluorescein lifetime from the assay on both the glass and silvered portions after 30 minutes incubation was measured, as well as after 30 seconds microwave heating, FIG. 8. Remarkably, the intensity decay curves for fluorescein after 30 minutes incubation as compared to 30 seconds low power microwave heating were almost identical, both revealing significantly reduced lifetimes as compared to the glass control. Interestingly, the glass control shows about 80 counts of background, which is due to the longer data acquisition times, a function of the lower S:N of fluorescein on glass as compared to silver. Given the now widespread use of fluorescence spectroscopy for protein structural and environmental information due to the sensitivity of fluorophores to their environment,[40] then it can be concluded from FIG. 8 that the assays are identical (both conformationally and environmentally), after both a 30 minute room temperature incubation and also after 30 seconds microwave heating. These intensity decay curves not only serve to confirm a modification in the fluorophore radiative decay rate, $\tau_m$, but indeed the feasibility of the MAMEF assay platform. It is also demonstrated that the assay does not undergo any protein conformational changes due to low power microwave heating, as evidenced by resonance energy transfer studies.

Fluorophore or analyte photostability is a primary concern in many applications of fluorescence, particularly platform type assays and in single molecule studies.[40,75] The maximum number of photons that are emitted by a fluorophore per second is roughly limited by its excited state lifetime.[40] Hence for shorter lifetimes, many more photons per fluorophore per second can typically be observed. This increased photon flux, which lends itself to much improved S/N ratios for assays and therefore improved detectability of analytes, manifests itself as the integrated area under the emission intensity curves of FIGS. 4 and 5. Clearly many more photons are emitted per fluorescein molecule in close proximity to silver. In addition to an increased detectability, a reduced lifetime in the presence of silver, affords for a greater fluorophore photostability, as fluorophores inherently spend less time in an excited state (reduced lifetime) and are therefore less prone to photo oxidation, the major photo destruction pathway for fluorescent probes.[40]

Figure 9:
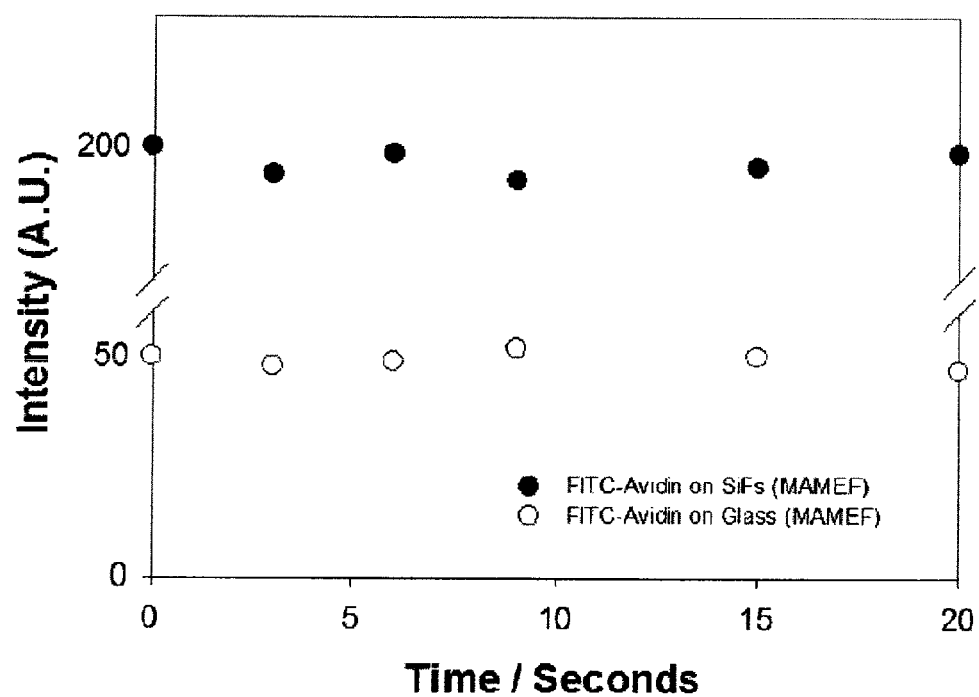
FIG. 9 shows fluorescein emission intensity from both silvered and glass substrates as a function of cumulative low power microwave heating. The fluorophore is unperturbed by the microwaves.

Subsequently, the photostability of the fluorescein based assay was studied after microwave heating to assess any degree of photo destruction, where the assay was firstly incubated for 30 minutes at room temperature. FIG. 9 shows the cumulative microwave heating of the assay, where the assay was heated and then the fluorescence intensity at 530 nm measured after 470 nm, about 30 mW excitation for 1 minute, the procedure then repeated. After 20 seconds microwave heating no change in fluorescein emission was evident on both the glass and silvered slides. In addition, no change in emission signal intensity was evident during the 1 minute exposure to laser light. Interestingly, while not shown in FIG. 9, under the conditions employed with this assay it took greater than 3 minutes microwave heating to dry the assay, up until which point, both the fluorescein emission spectra and peak intensity remained constant.

Figure 10:
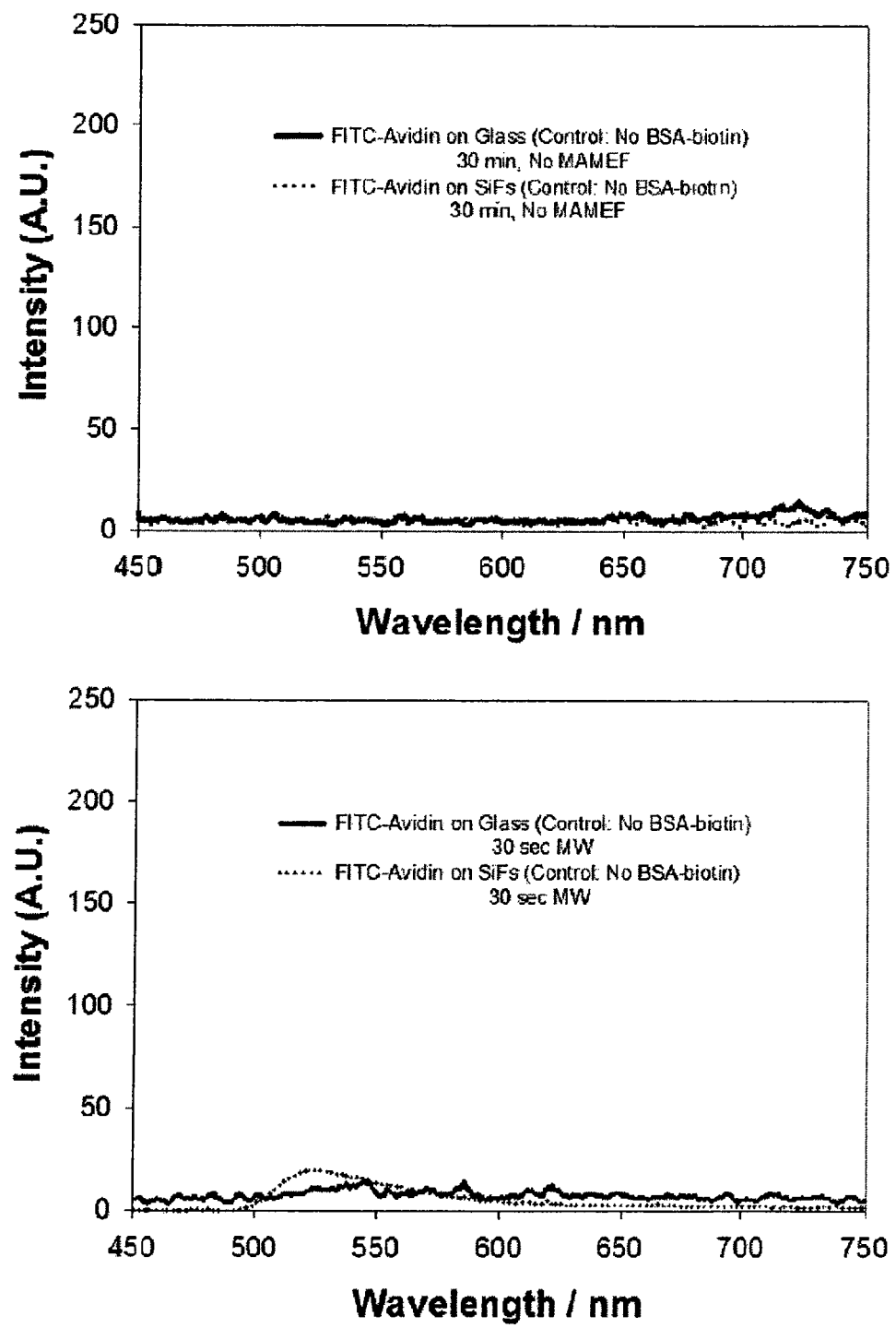
FIG. 10 shows the rate of control experiments of non-specific absorption of fluorescein-avidin to the bare surfaces after 30 minutes incubation (Top) and after 30 seconds low power microwave heating (Bottom). Both glass and silvered surfaces were not coated with biotinylated—BSA. Both plots show that the extents of non-specific absorption are indeed very low, and that low power microwave heating does not increase the extent of non-specific absorption.

As with most assays it is the bioactivity of the species and nature of the surfaces that govern the extent of non-specific reactions or non-specific surface assay absorption.[1-8] Subsequently, it was questioned whether the use of low power microwave heating would indeed increase the rate of nonspecific absorption in the presently described model assay. FIG. 10 shows the results of control experiments were both glass and silvered surfaces were incubated with fluorescein-labeled avidin. In these experiments the surfaces were not pre-coated with biotinylated-BSA. From FIG. 10—top it can be seen that after 30 minute incubation with no microwave heating, essentially no fluorescein was evident from the bare surfaces. This indicates that there is no non-specific absorption of fluorescein labeled avidin with the surface. However, after 30 seconds low power exposure to microwaves, a very small amount of fluorescein emission was evident on the SiFs. This amount was substantially lower than the >200 au fluorescence intensity shown in FIG. 5 top, and is therefore not thought to be of any significance. Subsequently, in the presently described model system, the extent of nonspecific absorption due to microwave heating was deemed negligible.

Figure 11:
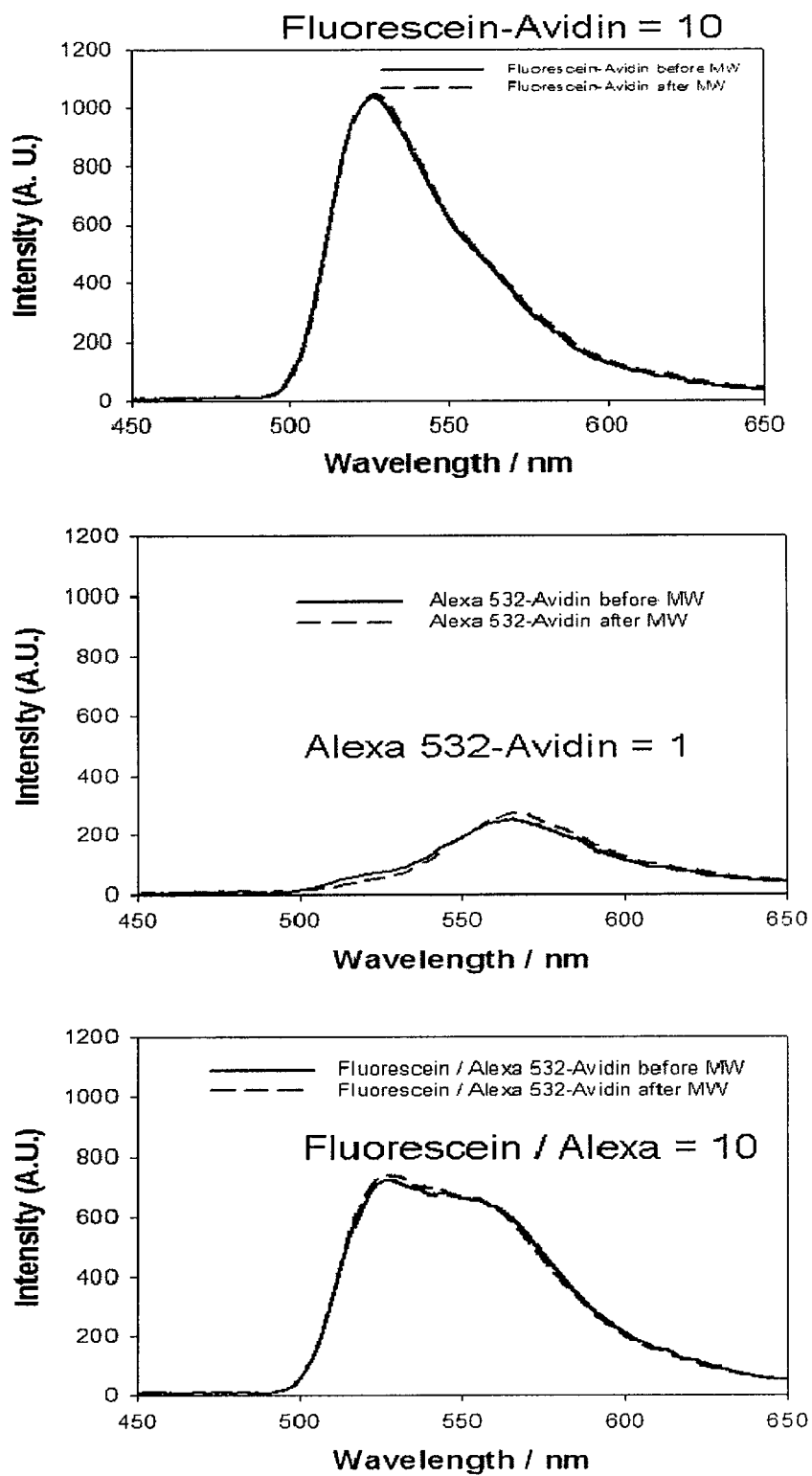
FIG. 11 shows the results of fluorescence resonance energy transfer experiments to confirm that low power microwaves do not denature the proteins. (Top)—Fluorescein (Donor) labeled avidin before and after low power microwave heating, (Middle)—Alexa 532 (Acceptor) labeled avidin before and after low power microwave heating, (Bottom)—Donor-acceptor labeled avidin (ratio D/A=10) before and after low power microwave heating. The extent of energy transfer does not change after heating, suggesting that the proteins are not denatured.

It was next investigated whether exposure to microwaves indeed caused protein denaturation in the present assay system. Protein conformational changes on the surface of a metal-enhanced fluorescence assay could potentially complicate assay kinetics and sensitivity, given that MEF is a through space and distance dependent phenomenon.[22,23,37] Subsequently, Fluorescence Resonance Energy Transfer (FRET) was employed to investigate any protein conformational changes, a technique which is widely used and therefore needs no introduction in this regard.[40] To investigate this, Fluorescein (Donor) and Alexa 532 (Acceptor) labeled avidin were incubated on surfaces both separately, together and both before and after microwave heating, FIGS. 11 and 12. In FIG. 11—top it can be seen that the emission spectral properties of fluorescein labeled avidin incubated onto a biotinylated-BSA surface both before and after microwave heating remain unchanged. Similarly the acceptor (Alexa 532) incubated alone on the biotinylated surface shows no change in its emission spectral properties, FIG. 11—middle. When both the donor and acceptor were incubated together (30 mins) on the surface with a D/A ratio of 10:1, then it can be clearly seen that both the Fluorescein emission and the Alexa emission, after sole excitation of the donor, FIG. 11—bottom. Interestingly, the emission spectra are identical both before and after microwave heating, suggesting that the surface protein assay has not undergone any conformational changes, where such changes would alter the FRET pair emission spectra.

Figure 12:
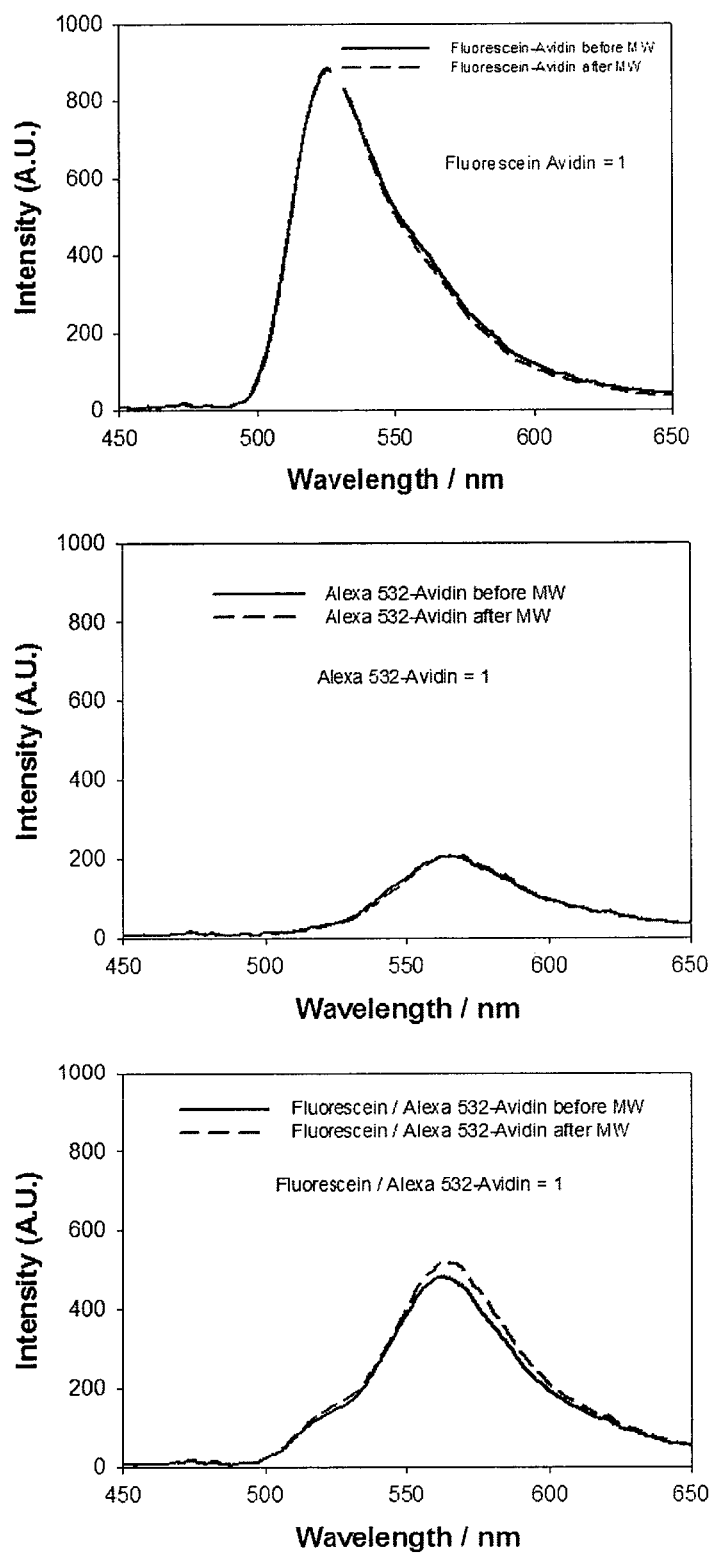
FIG. 12 shows the results of further fluorescence resonance energy transfer experiments to confirm that the proteins are not denatured by low power microwaves. (Top)—Fluorescein (Donor) labeled avidin before and after low power microwave heating, (Middle)—Alexa 532 (Acceptor) labeled avidin before and after low power microwave heating, (Bottom)—Donor-acceptor labeled avidin (ratio D/A=1) before and after low power microwave heating.

In FIG. 11—bottom the emission spectra is dominated by the fluorescein emission, primarily because this is in excess, a 10:1 donor:acceptor surface ratio. Subsequently, surfaces where the D/A ratio was 1:1 were prepared as shown in FIG. 12. Similarly to FIG. 11, the spectra for donor and acceptor alone are unperturbed by microwave heating. However, when the donor and acceptor are incubated together (30 mins), the spectra is no longer dominated by the donor emission, but instead significant energy transfer can be observed to the acceptor, FIG. 12—bottom. Again, after microwave heating, the spectra are almost identical to those not heated, suggesting that no protein conformational changes occur, by the fact that the extent of energy transfer remains constant, i.e. no D/A spectral changes. This strongly suggests that the present approach using low power microwave heating does not modify surface assay morphology.

The present inventor has demonstrated a low cost and simplistic approach to overcoming some of the classical physical constraints imposed by current assay platforms, namely assay rapidity and sensitivity.[1-8] The present MAMEF approach therefore has several notable advantages including:

- The fluorescence amplification provided by the silver nanostructures has been shown to be applicable to many fluorophores and therefore wavelengths, from the UV to near IR.[22,23,37] Hence, fluorophores currently employed in assays would still be suitable. However, the use of low quantum yield fluorophores would lead to much larger fluorescence enhancements (i.e. $1/Q_0$) and could significantly reduce unwanted background emission from fluorophores distal from the silvered assay, recalling that MEF is a close-range (<10 nm) through-space interaction.[22,23,37]
- The metal-enhanced fluorescence phenomenon has been shown to provide for increased emission intensities,[19-21] up to several thousand-fold.[32] This substantially increases detection limits (i.e. lower concentrations detectable), which is a major criterion in assay development today.[1-8]
- A whole variety of silvered surfaces can be routinely prepared, which do not require the benefits of a nanofabrication lab and sophisticated instrumentation such as electron beam lithography.[19-21]
- The reduced lifetime of fluorophores in close proximity to silver nanostructures provides for a substantially increased fluorophore photostability.[19-21] In addition, shorter lifetimes allow for higher fluorophore cycling rates,[19-21] also providing for increased fluorophore and therefore assay detectability.[19-21,41]

The Low power microwaves employed here do not perturb the silvered surfaces, do not produce "arcing" which is commonly observed for metallic objects in microwave cavities,[58] or even denature or change protein conformation. Low power microwaves provide for effective rapid heating of the assays, producing identical final fluorescence intensities, fluorophore lifetimes, as well as extents of energy transfer (protein conformation) as compared to room temperature incubation.

Materials

Bovine-biotinamidocaproyl-labeled Albumin (biotinlyated BSA), FITC-labeled avidin, silver nitrate (99.9%), sodium hydroxide (99.996%), ammonium hydroxide (30%), trisodium citrate, Dglucose and premium quality APS-coated glass slides (75×25 mm) were obtained from Sigma-Aldrich. Alexa 532-labeled avidin was obtained from Molecular Probes (Eugene, Oreg.). All chemicals were used as received.

Formation of Silver Island Films (SiFs) on APS-Coated Glass Substrates

In a typical SiF preparation a solution of silver nitrate (0.5 g in 60 ml of deionized water) in a clean 100-ml glass beaker, equipped with a Teflon-coated stir bar, is prepared and placed on a Corning stirring/hot plate. While stirring at the quickest speed, 8 drops (≈200 μL) of freshly prepared 5% (w/v) sodium hydroxide solution are added. This results in the formation of dark brown precipitates of silver particles. Approximately 2 ml of ammonium hydroxide is then added, drop by drop, to re-dissolve the precipitates. The clear solution is cooled to 5° C. by placing the beaker in an ice bath, followed by soaking the APS-coated glass slides in the solution. While keeping the slides at 5° C., a fresh solution of D-glucose (0.72 g in 15 ml of water) is added. Subsequently, the temperature of the mixture is then warmed to 30° C. As the color of the mixture turns from yellow-green to yellow-brown, and the color of the slides become green, the slides are removed from the mixture, washed with water, and sonicated for 1 minute at room temperature. SiFs-deposited slides were then rinsed with deionized water several times and dried under a stream of nitrogen gas.

SiFs-deposited glass slides were then coated with black electrical tape, which is attached to a self-sticking paper, containing three 5 mm wide circular holes (referred to as a "black body") on both the silvered and unsilvered slide, prior to the assay fabrication and subsequent fluorescence experiments.

Preparation of the Model Protein Assay (Biotin-Avidin) on Silver Island Films and on Glass (Control Assay)

Methods for preparing metal-enhanced fluorescence (MEF) have been previously described.[19-21] This experimental format has been adopted for two main reasons, the first, being that Human Serum Albumin (HSA) is known to bind to silvered surfaces and indeed forms a monolayer,[71-73] and secondly, the dimensions of the protein being such that the protein allows for a mean ≈4 nm separation of the silver and the fluorophore, MEF being a through space phenomenon, as demonstrated by the late T. Cotton.[19-21,76] In contrast, Surface Enhanced Raman Scattering (SERS) is known to be a consequence of mostly contact between the species of interest and the silvered surface.[76]

The model assay described herein is based on the well-known interactions of biotin and avidin. Biotin groups are introduced to the surface through biotinylated-BSA, which, similar to HSA, readily forms a monolayer on the surfaces of glass and SiFs.[71-73] Binding the biotinylated-BSA to the SiFs and the glass was accomplished by incubating 10 μM biotinylated-BSA solution in the "black-body" micro cuvettes for 1 hour, followed by rinsing with water to remove the unbound material. For the model assay, then 30 μl of 1 μM FITC-labeled avidin was subsequently added into the biotinylated-BSA coated glass and SiFs coated micro cuvettes, 30 minutes for the control experiments at room temperature (20° C.), and 20 seconds in the microwave cavity (0.7 cu ft, GE Compact Microwave Model: JES735BF, max power 700 W). The power setting was set to 2 which corresponded to 140 W over the entire cavity. In all the experiments performed with low power microwaves, using both glass slides and quartz cuvettes modified with the "black body," there was no evidence of surface drying.

Photostability Experiments

The effect of microwaves on the photostability of FITC was studied by exposing the model assay, which was previously allowed to run to completion at room temperature for 30 minutes, to microwaves for a cumulative total of 20 seconds. Approximately, 30 mW, 470 nm laser line excitation for 1 minute was used before the emission intensity was noted.

Fluorescence Resonance Energy Transfer (FRET) Experiments

FRET experiments[40] were undertaken to evaluate the effect of microwaves on protein conformation and thus denaturation. FITC and Alexa 532 were chosen as the donor-acceptor pair. Two different FITC to Alexa 532 ratios were studied on biotinylated-BSA coated glass slides that were covered with the same "black body" that was described hereinabove. 10:1 and 1:1 dilutions of FITCavidin and Alexa 532-avidin were incubated on biotinylated-BSA coated glass slides, which were then exposed to microwaves (power setting 2) for 20 seconds. Fluorescence spectra from the samples, both before and after microwave exposure, were taken.

Absorption, Steady-State and Time-Resolved Fluorescence Spectroscopy

All absorption measurements were performed using a Varian Cary 50 UV-Vis spectrophotometer. Temperature-dependent absorption measurements were performed using a Cary Single Cell Peltier accessory. Fluorescence measurements on SiFs were performed by placing the films on a stationary stage equipped with a fiber-optic mount on a 15-cm-long arm (normal to sample). The output of the fiber was connected to an Ocean Optics HD2000 spectrofluorometer to measure the florescence emission spectra. The excitation was from the second harmonic (470 nm) of the diodepumped Nd:YVO4 laser (compact laser pointer design, output power ≈30 mW) at an angle of 45 degrees. The emission was observed through a 500 nm long-pass filter (Edmund Scientific). Time-resolved intensity decays were measured using reverse start-stop time-correlated singlephoton counting (TCSPC) 40 with a Becker and Hickl gmbh 630 SPC PC card and an un-amplified MCP-PMT. Vertically polarized excitation at ≈440 nm was obtained using a pulsed laser diode, 1 MHz repetition rate.

Atomic Force Microscopy (AFM) and Real-Color Photographs

Atomic Force Microscopy (AFM) images of SiFs were collected using an Atomic Force Microscope (TMX 2100 Explorer SPM, Veeco) equipped with an AFM dry scanner (the scanning area was 100×100 mm) Surfaces were imaged in air, in a tapping mode of operation, using SFM non contact mode cantilevers (Veeco). The AFM scanner was calibrated using a standard calibration grid as well as by using gold nanoparticles, 100 nm in diameter from Ted Pella. Images were analyzed using SPMLab software. The real-color photographs of fluorophore labeled-BSA on SiFs were taken with an Olympus Digital camera (C-740, 3.2 Mega Pixel, 10× Optical Zoom) through the same long-pass filter that was used for the emission spectra.

Temperature Calibration in the Microwave Cavity

Figure 13:
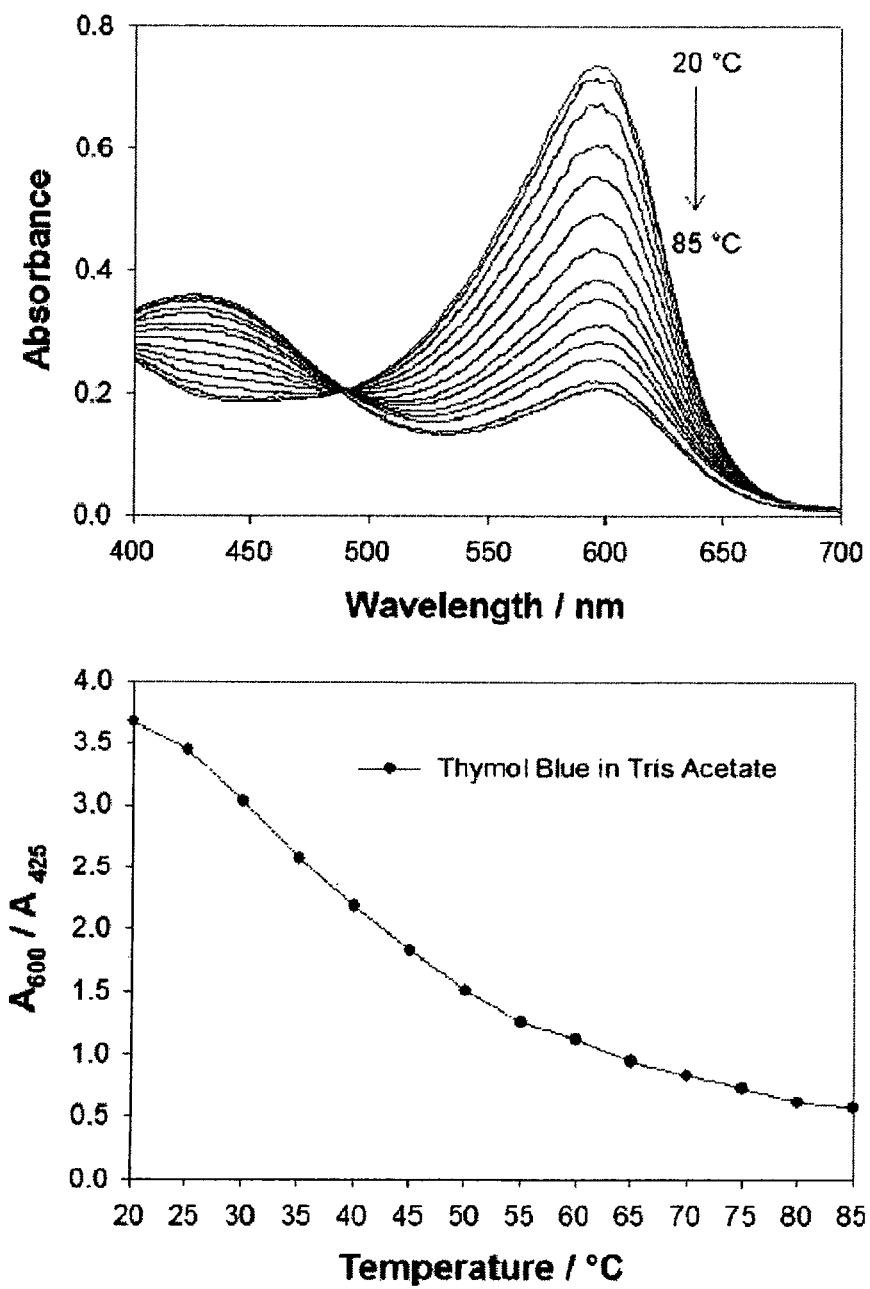
FIG. 13 shows thymol blue absorption spectra as a function of temperature (Top), and the subsequent ratiometric plot of the 600 and 425 nm absorption bands as a function of temperature (Bottom).

In order to calibrate the temperature change during low power microwave heating, a simple pH thermo-indicator system was used (0.5 mM Thymol Blue, in 50 mM Tris Acetate, pH 9.0). In this regard, 30 µl of a solution of Thymol Blue was placed in a quartz cuvette that was covered with the "black body," except for two parallel sides to allow the passage of light for absorption measurements. This arrangement was very similar to that employed on the glass and silvered assay slides. The absorption spectra of the sample were recorded as the temperature was gradually increased from 20 to 85° C., as shown in FIG. 13. The color of the solution changed with temperature from deep magenta to pale yellow, due to the temperature dependence of the ionization constant of the Tris buffer. As the temperature was increased, the pH of the solution is decreased and the distribution of the ionization states of the thymol blue dye changes resulting in a color change as a function of temperature. The reversible color change is readily observed in the UV-Vis spectrum via changes in the 425 and 600 nm spectral bands, FIG. 13-top.

Figure 14:
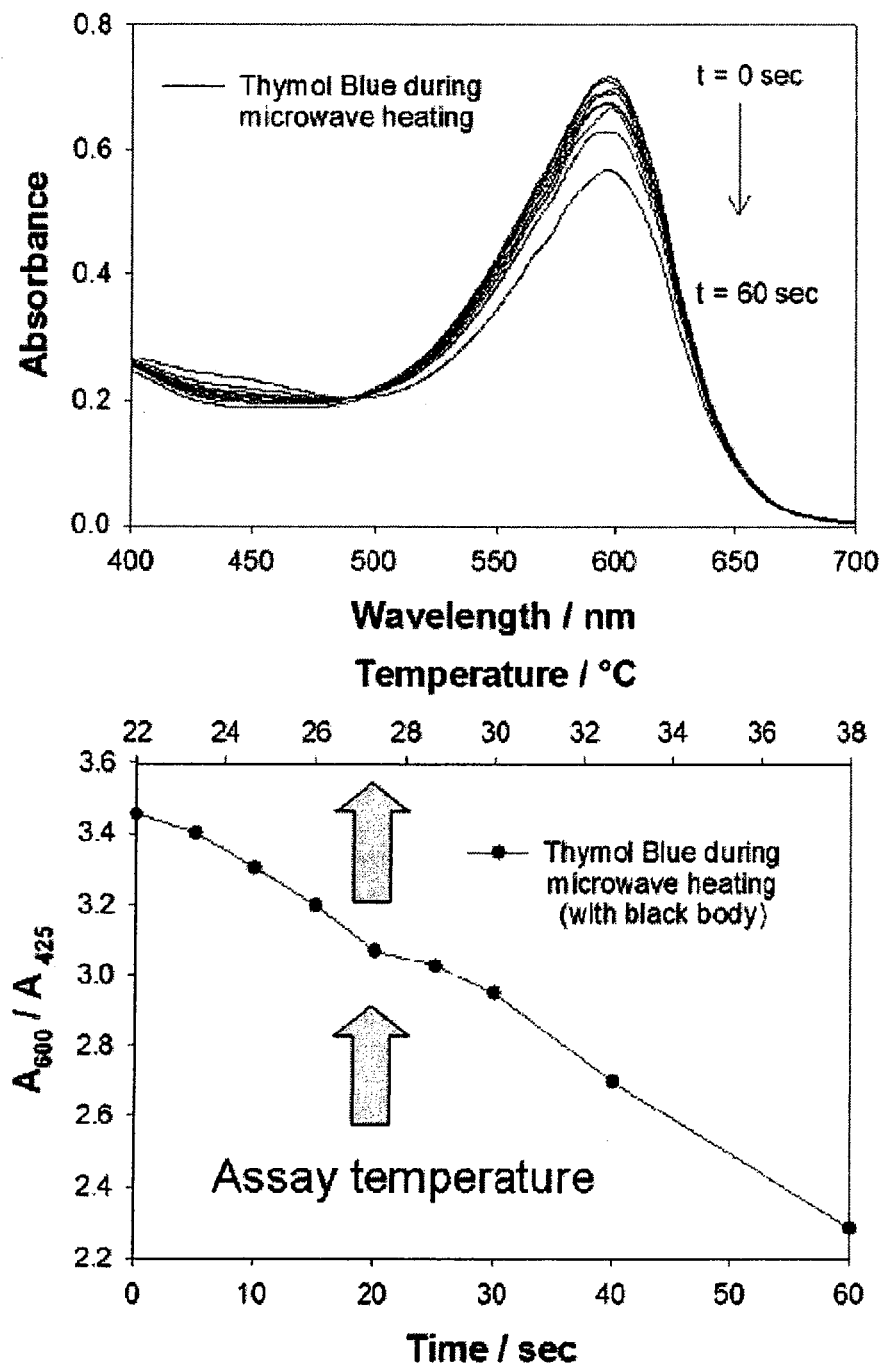
FIG. 14 shows absorption spectra as a function of temperature for 30 µl thymol blue in the black body sample holder (Top) and the respective absorbance, temperature Vs time ratiometric plot (Bottom).
Figure 15:
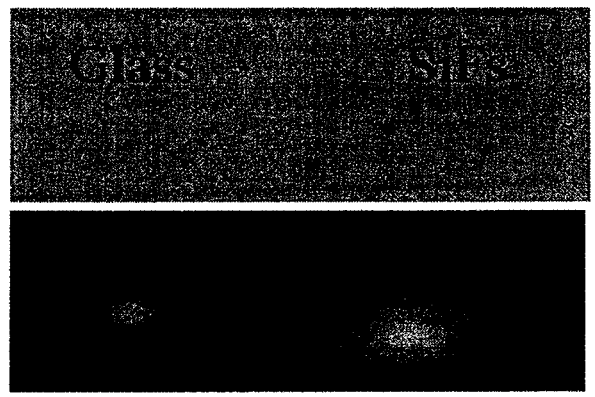
FIG. 15 shows TOC glass slides.

The calibration curve (A600/A425 vs. Temperature), FIG. 13—bottom, obtained from the abovementioned calibration measurements, was used to determine the temperature of the sample during the microwave process: the absorption spectra of 30 µl Thymol blue in a quartz cuvette covered with the same "black body" was recorded both before and after microwave heating for up to 60 seconds, FIG. 14—top, where the both the volume used and the black body were the same as actually used in the assays. The ratiometric response (A600/A425) obtained from these samples, FIG. 14—bottom, was used to determine the temperature of the sample during microwave heating from the calibration curve. From calibration plots, a 20 second 140 W, 2450 MHz microwave exposure, resulted in a temperature jump of approximately 80° C. (to about 28° C.) for 30 µl of sample. Hence, with this calibration curve, the assay surface temperature could be easily changed.

20 Seconds of microwave heating roughly corresponded to a 8-10° C. temperature jump.[32] It should be noted that a commercially available instrument (The Biowave), which is also based on low power microwaves but uses a thermocouple temperature probe, is available from Ted Pella, CA. This instrument, while inevitably less time consuming with respect to the needed calibration steps undertake here, is substantially more costly than the simple approach undertaken in this paper.

Using a Black Body for Assay Temperature Control

To achieve microwave power tunability and therefore assay temperature and completion time flexibility, we employed black electrical tape to construct small micro cuvettes, which held ≈30 µL of fluid on the surface of both the bare and silvered glass, a volume typically used in high throughput assays.[1-8] It was found that the presence of the "black body" had the desirable effect of substantially reducing the local cavity power, where without the black body micro cuvettes, 30 µL of surface fluid quickly boiled and dried at 140 W. In essence, the use of the black bodied micro cuvettes, afforded cavity power tunability between the number 1 and 2 settings on the microwave device, alleviating the need for spending large monies on a tunable commercial instrument.

Myoglobin Immunoassay

To address assay rapidity the use of low power microwaves (2450 MHz) was employed to heat the samples. Interestingly, metallic particles in the microwave cavity appear to be preferentially heated as compared to solvents, which advantageously localizes both the MEF effect and heating around the silver nanostructures. For metals, the attenuation of microwave radiation, arises from the creation of currents resulting from charge carriers being displaced by the electric field.[93] These conductance electrons are extremely mobile and unlike water molecules can be completely polarized in $10^{-18}$ s. In the microwave cavity, the time required for the applied electric field to be reversed is far longer than this, in fact many orders of magnitude. If the metal particles are large, or form continuous strips, then large potential differences can result, which can produce dramatic discharges if they are large enough to break down the electric resistance of the medium separating the large metal particles. Interestingly, and most appropriate for our new assay platform described here, small metal particles do not generate sufficiently large potential differences for this "arcing" phenomenon to occur. However, the charge carriers, which are displaced by the electric field, are subject to resistance in the medium in which they travel due to collisions with the lattice phonons.[93] This leads to Ohmic heating of the metal nanoparticles in addition to the heating of any surface solution-phase polar molecules.

Figure 16:
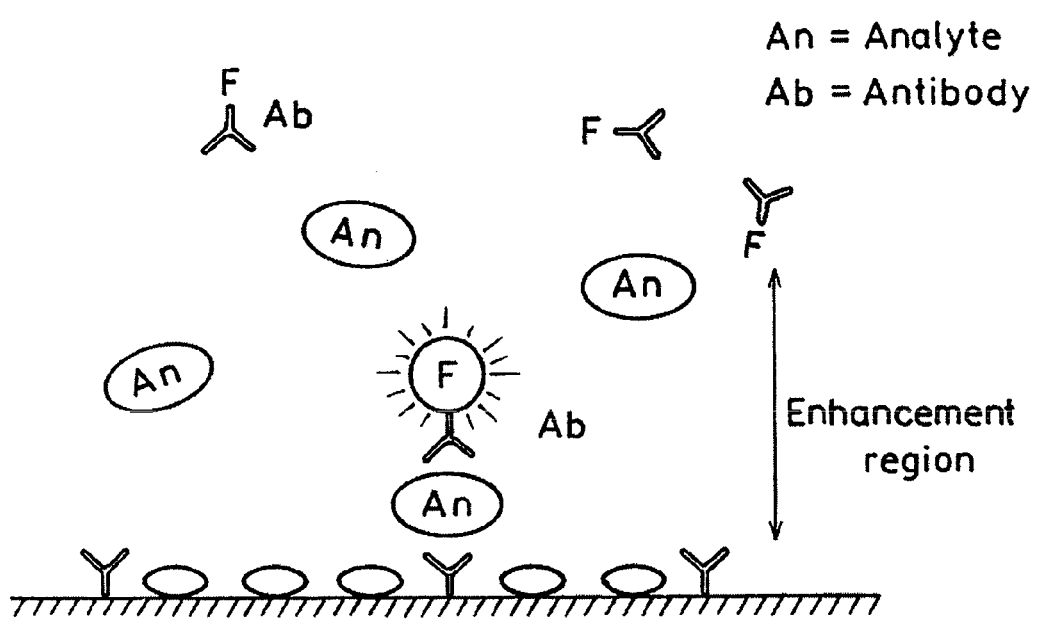
FIG. 16 shows a model metal-enhanced fluorescence immunoassay. A silvered surface features immobilized antibodies for a particular analyte. Upon formation of the sandwich Immunoassay, the low quantum yield fluorophore is brought into close proximity to the surface (within the 10 nm enhancement region), the system becoming highly luminescent and facilitating analyte detectability.

Immunoassays using the principals of the present invention and the MEF phenomenon are well-suited for use with low quantum yield fluorophores as shown in FIG. 16. This occurs due to:

The maximum metal-fluorophore system fluorescence emission enhancement and therefore analyte detectability, is roughly given by $1/Q_0$, where $Q_0$ is the quantum yield of the fluorophore alone in the absence of metal and hence low quantum yield fluorophores are more suited; and Low quantum yield fluorophores will invariably produce greater S/N ratios. This is because the MEF phenomenon is a through space phenomenon, occurring up to about 10 nm from the surface. Hence, low quantum yield material distal from the metal surface and outside the enhancement region, contributes little to background unwanted fluorescence.

Silver nitrate (99.9%), sodium hydroxide (99.996%), ammonium hydroxide (30%), trisodium citrate, D-glucose and premium quality APS-coated glass slides (75×25 mm) and bovine serum albumin (BSA) were obtained from Sigma-Aldrich. Myoglobin (recombinant) and monoclonal anti-myoglobin antibodies (capture anti-Myo antibodies clone 2mb-295, reporter anti-Myo antibodies clone 9mb-183r) were obtained from Spectral Diagnostics, Canada. All chemicals were used as received.

Reporter anti-Myo antibodies were labeled with Alexa Fluor-647 using a labeling kit from Molecular Probes; the kit provided dyes with reactive succinimidyl ester moieties, which react effectively with the primary amines of proteins.

Silver Island Films were formed as described previously, hereinabove. In a typical SiFs preparation, a solution of sodium hydroxide and ammonium hydroxide are added to a continuously stirred solution of silver nitrate at room temperature. Subsequently, the mixture is cooled down in an ice bath, Silane-Prep™ glass slides (Sigma) are inserted and a solution of D-glucose is added. As the temperature is increased, the color of the mixture turns yellow-brown and the SiFs-deposited slides are removed from the mixture, washed with water, and sonicated for 1 minute at room temperature. The effects of microwaves on SiFs were investigated by optical absorption spectroscopy and atomic force microscopy.

Figure 18:
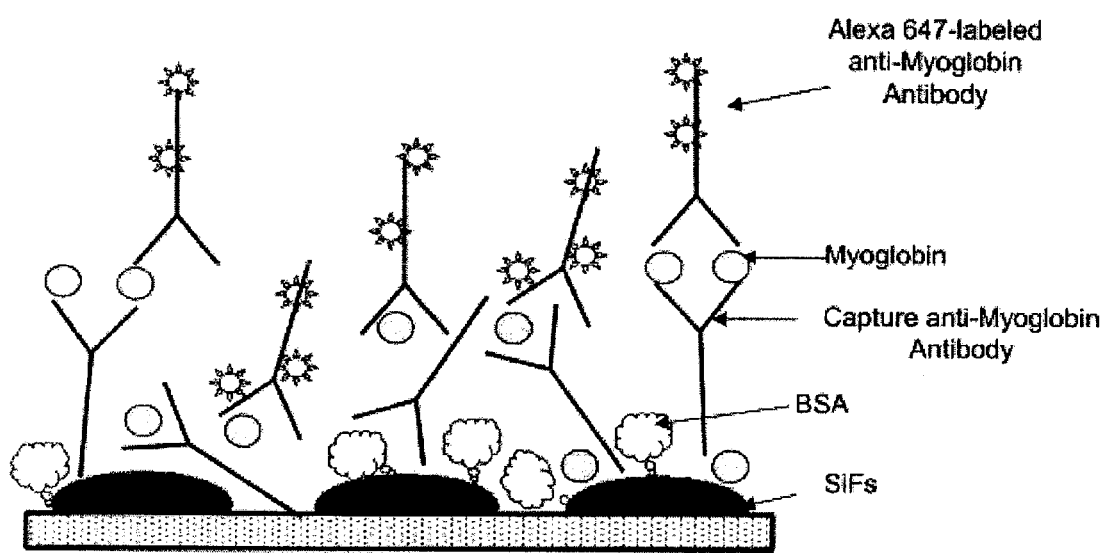
FIG. 18 shows a metal-enhanced fluorescence Myoglobin immunoassay of the present invention.

Myoglobin (Myo) immunoassays were performed in a sandwich format but with a few modifications, and as shown in FIG. 18. In this regard, slides were non-covalently coated with capture anti-Myo antibody at room temperature. The glass/SiFs surfaces were blocked with BSA in order to minimize the non-specific interaction of the antibodies and myoglobin with the surfaces. These surfaces were then incubated with Myoglobin antigen (100 ng/mL) at room temperature, and then used for end-point measurements. The end-point measurements were performed by incubating the antigen-coated surfaces in a solution of Alexa 647-labeled anti-Myoglobin Antibody for 30 minutes at room temperature, or by microwaving the antigen-coated surfaces with Alexa 647-labeled anti-Myoglobin Antibody for 20 seconds. Fluorescence measurements were performed by collecting the emission intensity at 45 degrees to the excitation through a long pass filter, using a Fiber Optic Spectrometer (HD2000) from Ocean Optics, Inc.

Figure 17:
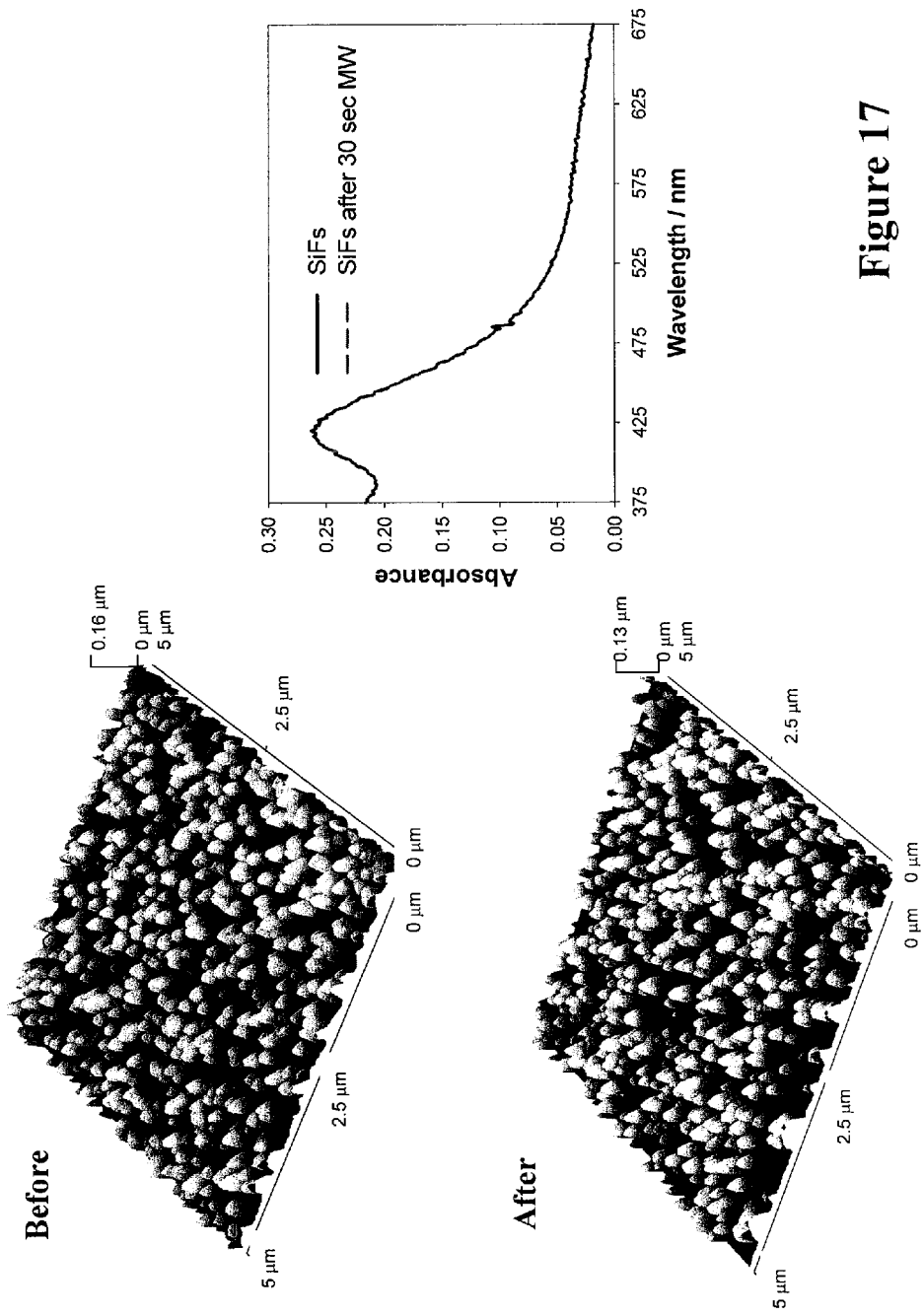
FIG. 17 shows AFM images both before and after microwave heating (Top left and Bottom respectively) and the corresponding plasmon absorption spectrum (right).

FIG. 17 shows the plasmon absorption spectra and AFM images of Silver Island Films (SiFs), both before and after low power microwave heating for 30 seconds. The cavity power was approximately 140 watts. As can be seen from FIG. 17, right, the microwaves and heating had no effect on the surface plasmon absorption of the SiFs, indicating no structural or surface silver shape changes, where the surface plasmon absorption is well-known to be characteristic of the shape of the nanoparticles, which is due to the mean free path oscillation of surface charges.[63,64] Further, no "sparking" was evident from the silvered surfaces, a known consequence of surface charge build-up and dissipation for larger sized particles or continuous surfaces.

The structural morphology of the silvered surfaces was measured both before and after low power microwave heating using Atomic Force Microscopy, as shown in FIG. 17 Left. While it is was somewhat difficult to probe the exact same area after microwave heating, very little, if no change in surface morphology was observed between the locations. No evidence for surface structural changes was found by microwave heating, clearly demonstrating the compatibility of the nanostructured surfaces to microwave exposure and therefore heating. In addition, control experiments were performed to investigate both the absorption and emission intensity of Alexa-647 (fluorophore stability) upon exposure to microwaves. Similarly to the silvered surfaces, the Alexa-647 was unperturbed.

In a clinical setting there are several assays that could significantly benefit from both rapidity and sensitivity. One particular assay is for the determination of myoglobin and its role in the clinical assessment of a myocardial infarction. A myoglobin assay is shown in FIG. 18. In addition, a control assay was prepared that was identical to the silvered myoglobin assay except that the control assay had no silver and was constructed on bare glass. This was constructed to rationale the benefits of using the MAMEF technique.

Figure 19:
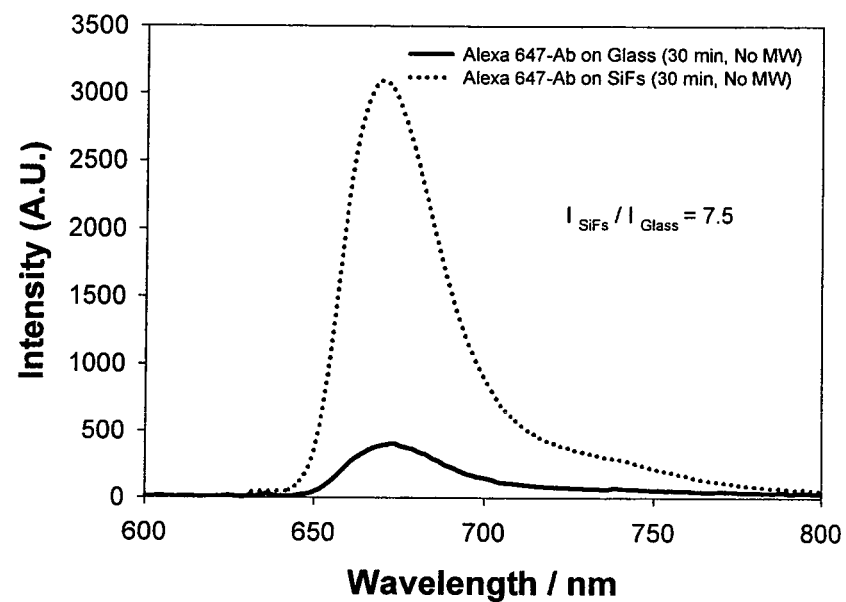
FIGS. 19 A and B show the fluorescence intensities of the myoglobin immunoassay in the presence and absence of silver with no microwave heating A (top) and after low power microwave heating B (top). The spectra on both glass and silver were found to be identical after normalization A and B (bottom).
Figure 19:
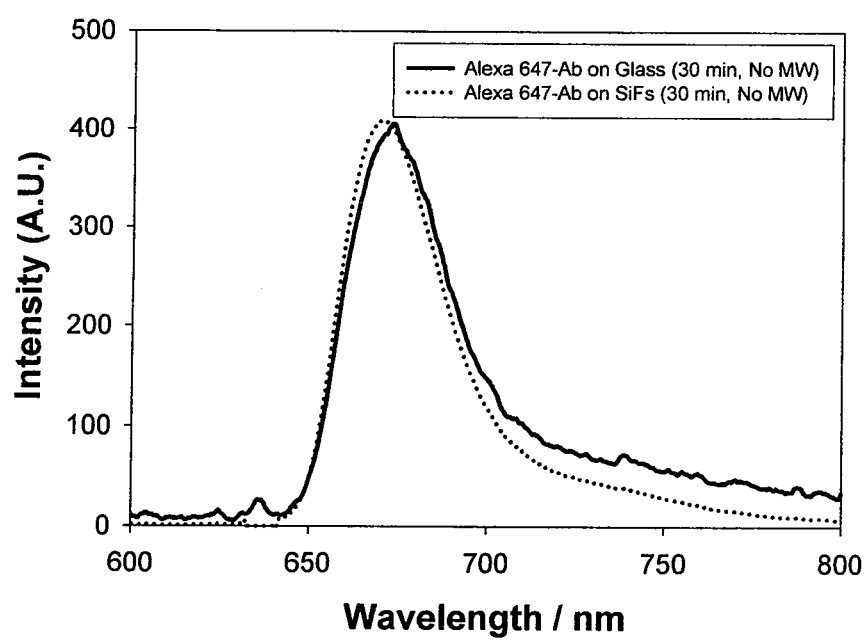
Figure 19:
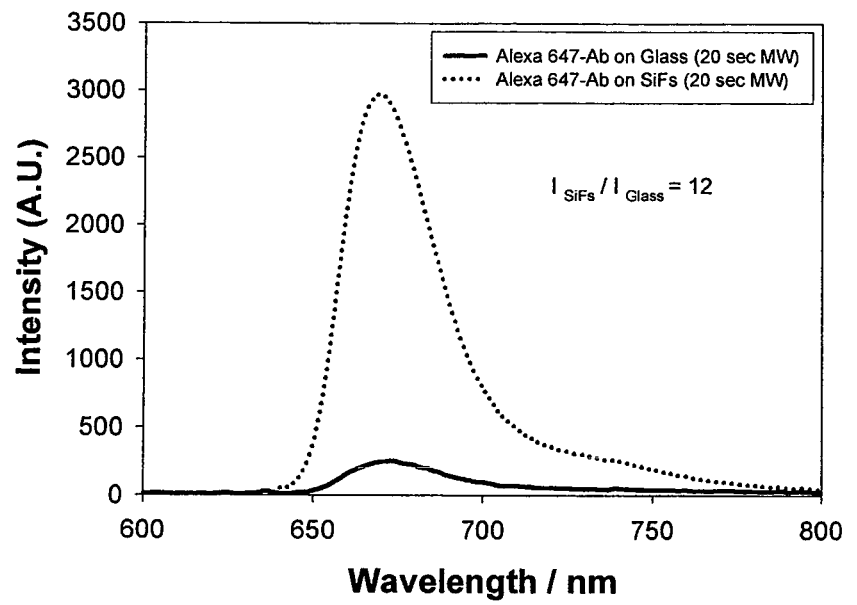
Figure 19:
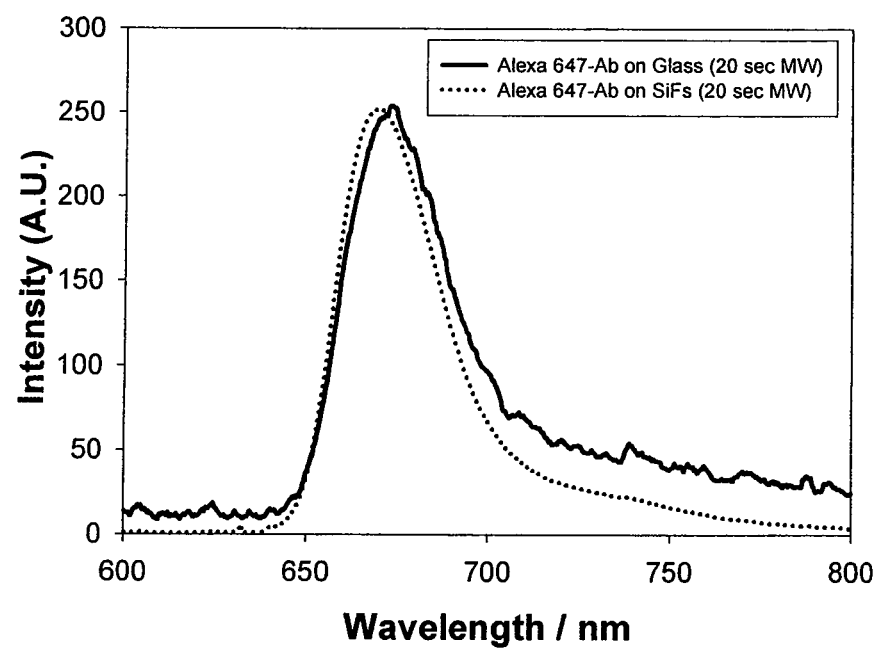

FIG. 19 A (top) shows the Alexa-647 emission intensity, both on silver and glass after 30 minute incubation and with no microwave heating. 100 ng/ml of myoglobin was used to sandwich the immunoassay, which is the clinical cut-off concentration for the assessment of a myocardial infarction. The emission spectrum, which was collected through a long-pass filter, shows an approximate 7.5-fold greater intensity from the silver as compared to the glass control. This effect is due to an apparent radiative decay rate modification of the fluorophore as it is brought into close proximity to the silver nanostructures upon formation of the sandwich immunoassay.

FIGS. 19 A and B show the fluorescence intensities of the myoglobin immunoassay in the presence and absence of silver with no microwave heating A (top) and after low power microwave heating B (top). The spectra on both glass and silver were found to be identical after normalization A and B (bottom). The sample was incubated for 30 minutes at room temperature, which was predetermined to be sufficient enough time to allow the assay to go to >95% completion.

FIG. 19 B shows the combined effect of both low power microwave heating and the optical amplification due to the silver for an identical immunoassay. Remarkably, the myoglobin immunoassay yields a similar final fluorescence intensity after 20 seconds microwave heating (Mw), ≈3000 arbitrary units, as compared to a 30 minute incubation, but with no microwave heating, FIG. 19 A. In addition, the silver still maintains its ability to optically amplify the Alexa-647 fluorescence emission after microwave heating.

A close inspection of both FIGS. 19 A and B reveals that the final fluorescence intensities on glass are different, which manifests itself in different fluorescence enhancement factors for both the assays. i.e. the enhancement is 7.5-fold with no microwave heating and 12-fold after low power microwave heating. The detailed temperature studies of the assays have revealed that the bulk temperature jump in the system was only 8° C. after microwave exposure (50 μL of sample), which does not account for the 90-fold increase in assay rapidity. It is theorized that this effect is due to the preferential localized heating around the silver nanostructures, rapidly accelerating mass transport to the surface and therefore the kinetics of the assay.

For the myoglobin assay described here, the use of MAMEF unexpectedly provided for a 12-fold increase in fluorescence detectability (emission intensity) which can easily be translated into assay sensitivity, and a 90-fold increase in rapidity, the assay being kinetically complete (100%) within 30 seconds of microwave heating.

In clinical settings, a myoglobin immunoassay can take over 1 hr to get an answer. This is due to the need to separate blood and the time required to run the serum assay to completion. The method described herein provides a platform technology which amplifies and kinetically increases assays to completion within a few seconds, potentially safeguarding life.

High Throughput Screening

Materials used include Silver nitrate (99.9%), trisodium citrate, Bovine-biotinamidocaproyl-labeled Albumin (biotinlyated BSA), FITC-labeled avidin and SigmaScreen™ Poly-D-Lysine coated High Throughput Screening (HTS) plates (96 wells) were obtained from Sigma-Aldrich.

The synthesis of silver colloids was performed using the following procedure: 2 ml of 1.16 mM trisodium citrate solution was added drop wise to a heated (90° C.) 98 ml aqueous solution of 0.65 mM of silver nitrate while stirring. The mixture was kept heated for 10 minutes, and then it was cooled to room temperature.

Figure 20:
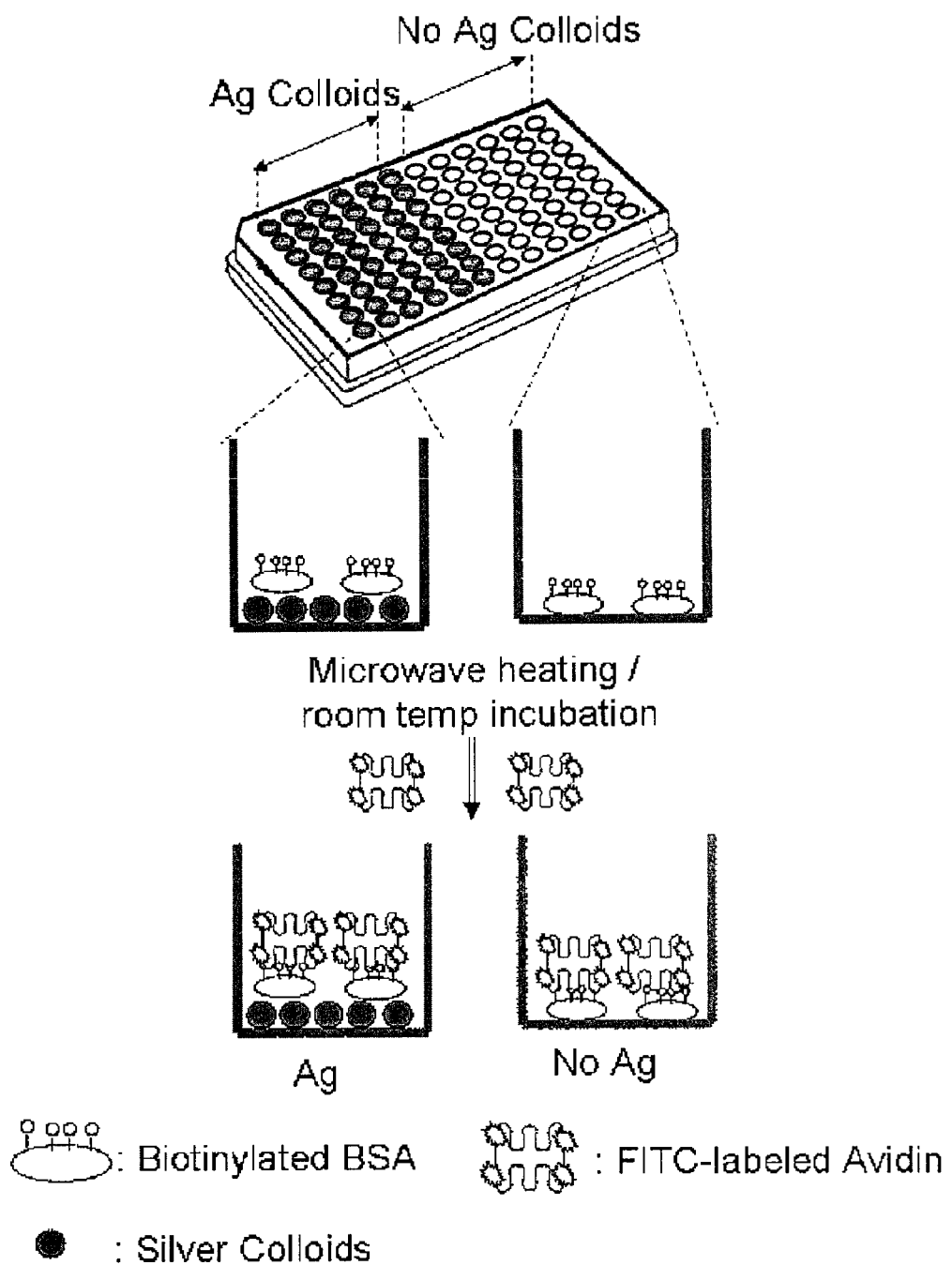
FIG. 20 shows the sample geometry in High Throughput Screening (HTS) wells.

The coating of the HTS plates was achieved by incubating 0.5 ml of silver colloid solution inside the HTS wells (48 wells) overnight. The HTS wells were coated with silver colloids due to the binding of silver to the amine groups of the surface molecule,[93,25] as shown in FIG. 20. The other half of the wells (48 wells) in the same HTS plates were left intentionally blank for the control experiments. The silver colloid deposited HTS wells were rinsed with deionized water several times prior to the fluorescence experiments. The number density of the silver colloid can be determined by the incubation conditions, the colloid size determined by the experimental conditions of preparation, all monitored by measuring the surface plasmon absorption, FIG. 22.

Biotin groups are introduced to the surface through biotinylated-BSA, which readily forms a monolayer on the surface of glass and silver colloid films.[71-73] Binding the biotinylated-BSA to the silver colloid-modified and unmodified part of the HTS wells was accomplished by incubating 10 μM biotinylated-BSA solution in the wells for 1 hour, followed by rinsing with water to remove the unbound material. For the model assay, then 100 μl of 1 μM FITC-labeled avidin was subsequently added to the biotinylated-BSA coated wells, 30 minutes for the control experiments at room temperature (20° C.), and 30 seconds in the microwave cavity (0.7 cu ft, GE Compact Microwave Model: JES735BF, max power 700 W), followed by rinsing with water to remove the unbound material. The power setting was set to 2 which corresponded to 140 W over the entire cavity. In all the experiments performed with low power microwaves using HTS plates, there was no evidence of drying of the aqueous media.

Several control experiments were also performed on the silver colloid-modified and unmodified HTS wells to investigate the extent of non-specific binding of proteins to the HTS wells including:

Incubation of FITC-avidin without Biotinylated-BSA and without microwave heating for 30 minutes,
Incubation of FITC-avidin without Biotinylated-BSA and without microwave heating for 30 seconds,
Incubation of FITC-avidin with microwave heating and without Biotinylated-BSA for 30 seconds.

Figure 21:
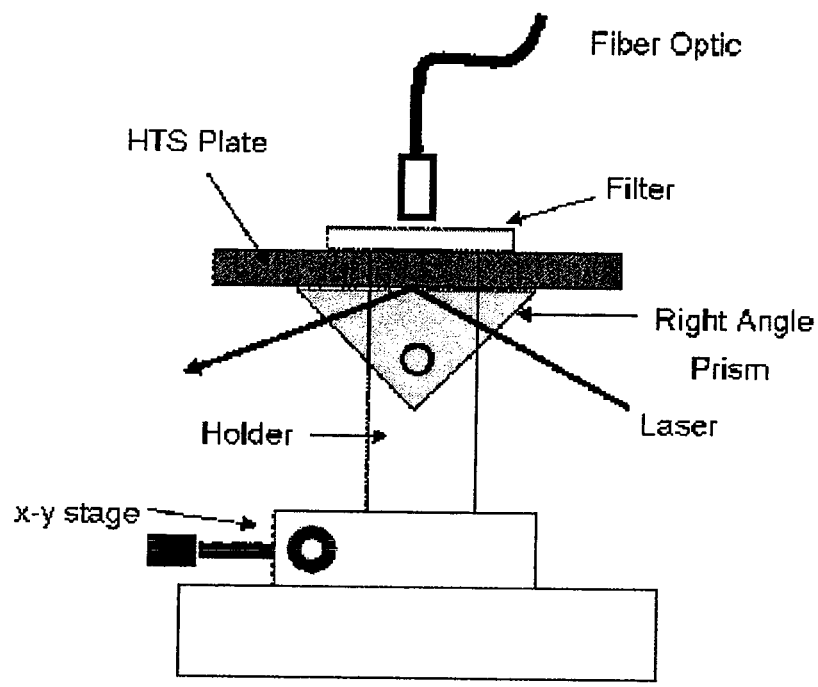
FIG. 21 shows a Total Internal Reflection Fluorescence TIRF experimental set-up mounted on an XY stage, for analysis of both the silvered and unsilvered HTS wells.

All absorption measurements were performed using a HP 8453 UV-Vis spectrophotometer. Fluorescence measurements on HTS plates were performed by placing the HTS plates on a Total Internal Reflection (TIR) stage equipped with a fiber-optic mount on a 15-cm-long arm (normal to sample), as shown in FIG. 21. The output of the fiber was connected to an Ocean Optics HD2000 spectrofluorometer to measure the fluorescence emission spectra. The excitation was from the second harmonic (473 nm) of the diode-pumped Nd:YVO4 laser (output power 30 mW) at an angle of 45 degrees. This configuration allowed easy changes of the incident angle and the evanescent excitation spot position. The emission was observed through a 500 nm razor-edge filter (Semrock).

The enhancement ratio $I_{SiFs}/I_{HTS}$ (the benefit of using MEF) is the fluorescence intensity observed on the silver colloids divided by the intensity on the non-silvered substrate. In addition, this model protein system as shown in FIG. 20, positions the fluorophore (which is fluorescein labeled avidin), from about 4 nm to about 10 nm from the surfaces.

Figure 22:
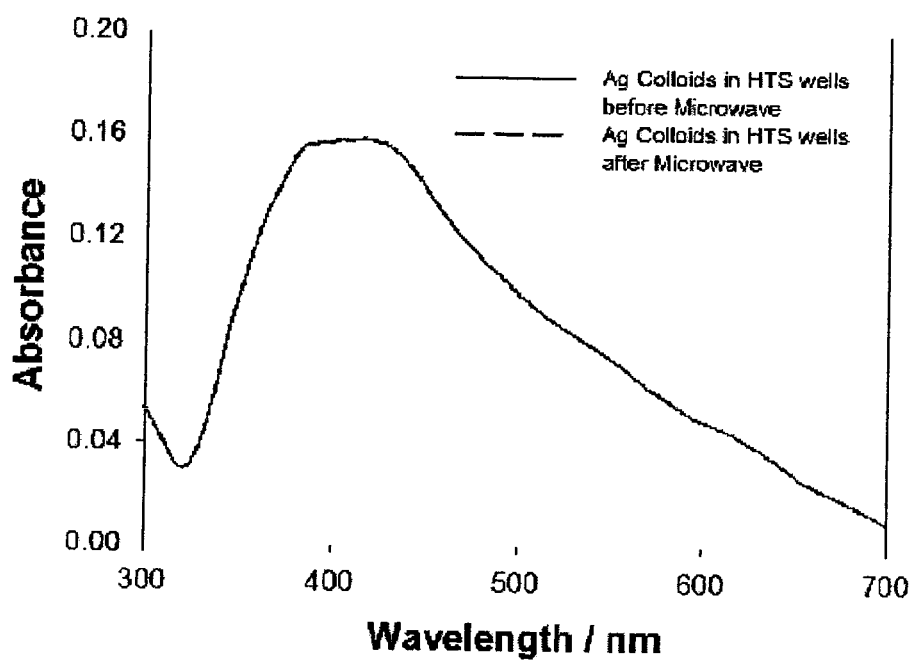
FIG. 22 shows the absorption spectra of silver-colloid coated plastic-bottomed HTS wells, before and after low power microwave heating.

For excitation of the assay shown in FIG. 20, Total Internal Reflection Fluorescence (TIRF)[41] was used. TIRF is an approach that readily allows the selective excitation of fluorophores within ≈200 nm proximity to surfaces, an approach ill used for surface assays. However, in the presence of silver islands as shown in FIG. 22, the evanescent field generated using the TIRF format, has been shown to much stronger than as compared to uncoated glass,[66] penetrating further into solution. Subsequently, evanescent wave excitation confines the excitation volume at the assay surface, eliminating the need for washing the solution from above the assay. Interestingly, because the MEF phenomenon only occurs out to about 10 nm from the silver nanoparticles, then unwanted background fluorescence from assay material distal from the surface is not observed, increasing the S/N in the HTS wells for sensing.

FIG. 22 shows the plasmon absorption spectrum of silver colloids deposited at the bottom of HTS wells, both before and after low power microwave heating for 30 seconds, wherein the cavity power was ≈140 watts. It is evident from FIG. 22, that the microwaves had no effect on the surface plasmon absorption of the silver colloids, strongly indicating no surface silver shape or size changes, where the surface plasmon absorption is well-known to be characteristic of the shape and size of noble metal nanoparticles.[20] Notably, large particles or even continuous metallic surfaces produce "sparking" when heated in microwave cavities. This effect is due to the charge build up, and subsequent "arching" as charge builds between the particles.[58] However, for the nanostructures deposited in the HTS wells described here, no sparking was evident at all, suggesting that the charge build up on the nanometer sized colloids is too small to induce dielectric breakdown of the medium separating them.

Figure 23:
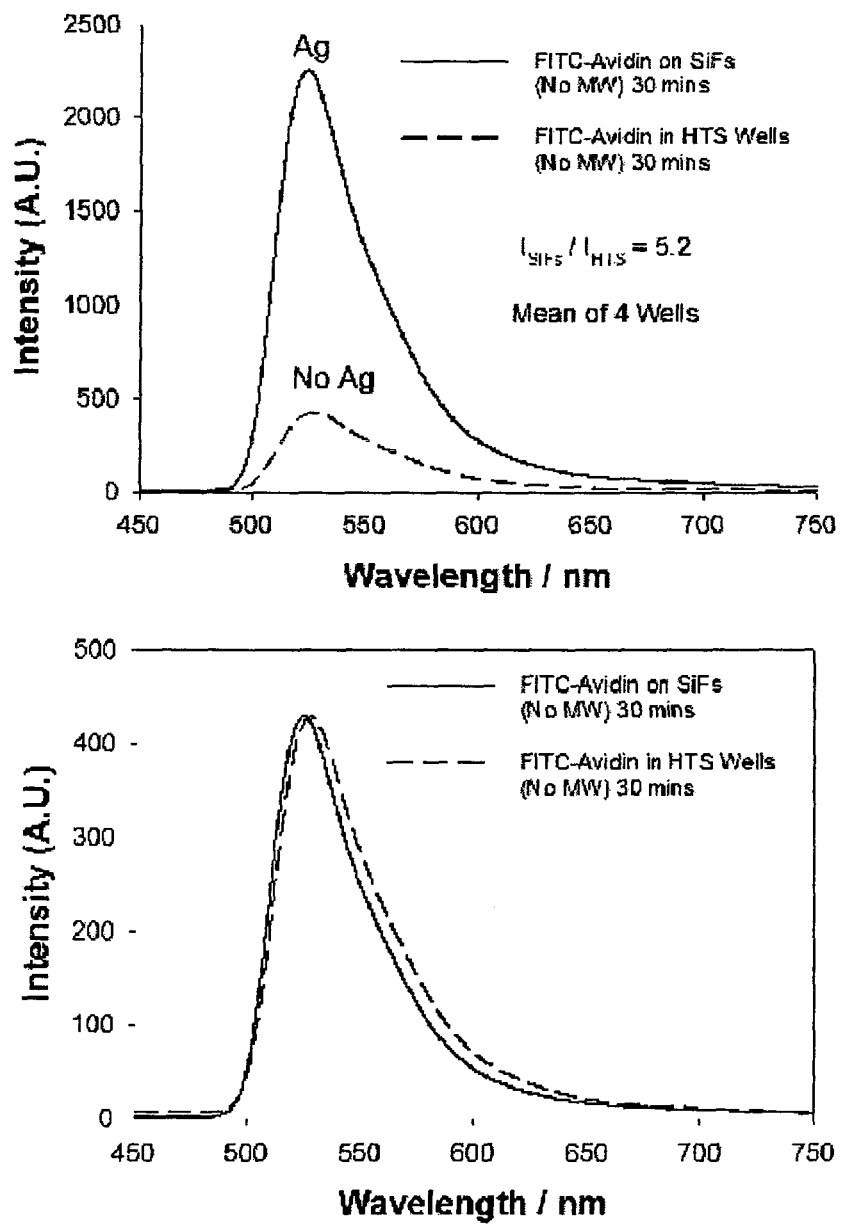
FIG. 23 shows fluorescence emission intensity of fluorescein from both silvered and non-silvered HTS wells (Top) after 30 mins room temperature incubation. The spectra are the average of 5 wells. (Bottom)—Normalized spectra from both silvered and non-silvered wells.

FIG. 23 shows the fluorescein emission intensity from both silvered and non-silvered HTS wells after room temperature incubation of the assay. The assay was incubated for 30 mins The emission, which was collected through a 500 nm razor edge filter (Semrock), shows an approximate 5 fold greater intensity from the silver as compared to the non-silvered wells. These values were the mean of 4 wells each, the data quickly collected from each well by moving the plate well on the XY stage as shown FIG. 21. This increase is not due to reflected photons from the silvered surface, i.e. scattering, but is in fact a consequence of a new near-field fluorescence phenomenon, whereby fluorophores in close proximity (<10 nm) to a silver nanostructures can be made highly fluorescent. FIG. 23 (bottom) shows almost identical spectra after normalization from both the silvered and non-silvered wells, indicating the only differences in emission being the relative intensities.

Figure 24:
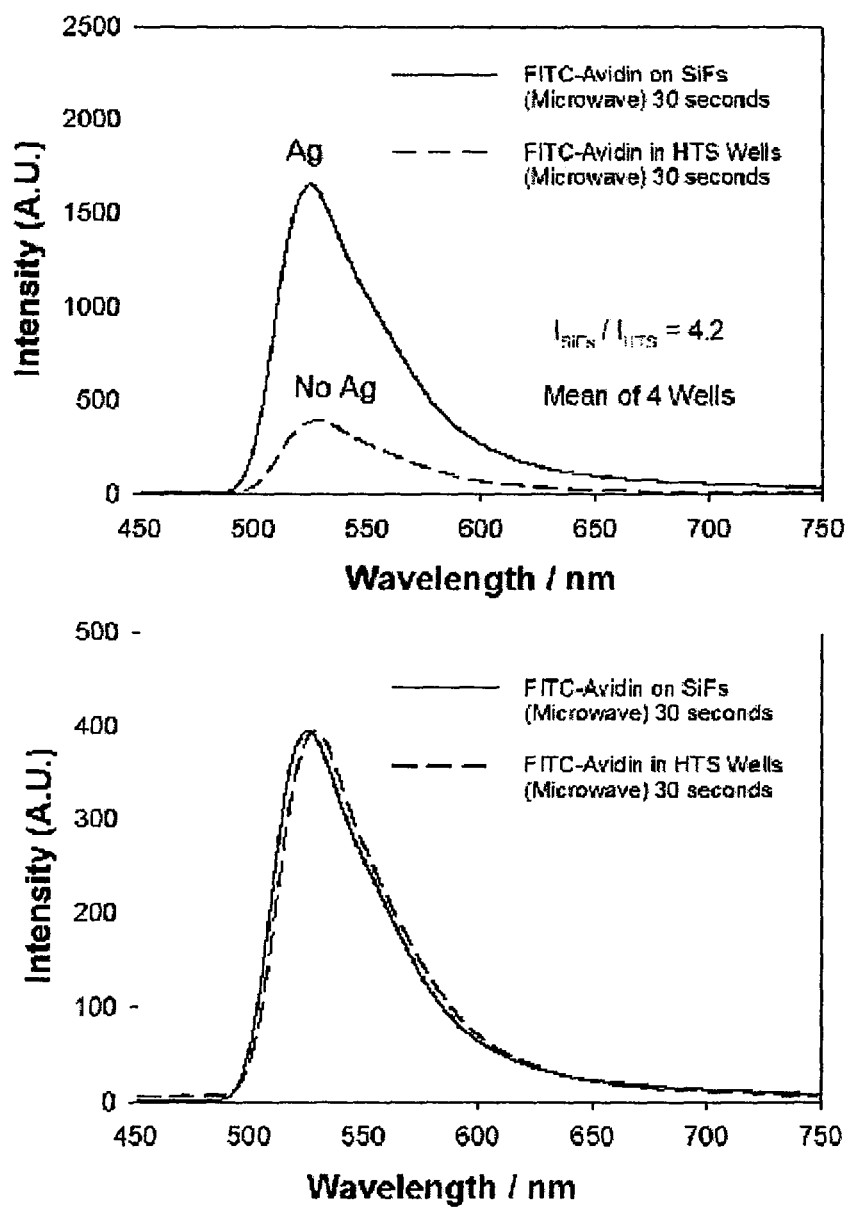
FIG. 24 shows fluorescence emission intensity of fluorescein from both silvered and non-silvered HTS wells (Top) after 30 seconds microwave heating. The spectra are the average of 5 wells. (Bottom)—Normalized spectra from both silvered and non-silvered wells after microwave heating.

FIG. 24 shows the fluorescence intensity of fluorescein from both the silvered and non-silvered HTS wells after 30 seconds microwave heating. Similar to FIG. 23, a ≈4-5 fold fluorescence enhancement can be seen on silver as compared to the non-silver wells. Interestingly, similar emission intensities were observed for 30 minutes incubation as compared to 30 seconds microwave heating, an ≈90-fold kinetic increase. The slight differences in the final fluorescence intensities (1700 vs. 2250 arbitrary units) are due to the fact that 45 seconds of heating was actually required to take the assay to >95% kinetically complete and not 30 seconds as shown in FIG. 24 top (data not shown). Interestingly, the emission intensity on the unsilvered plates was similar for both 30 minutes incubation and 30 seconds low power microwave heating. Clearly, by considering both FIGS. 23 and 24 top, the benefits of using low power microwave heating to accelerate assays in HTS wells can be seen as well as the combined benefit of amplified fluorescence to facilitate detection by the presence of the silver colloids. Surprisingly, the ≈90-fold kinetic increase can not be explained by just the ≈8° C. temperature jump, but instead it is thought that localized and indeed preferential heating on an around the silver nanoparticles occurs.

Figure 25:
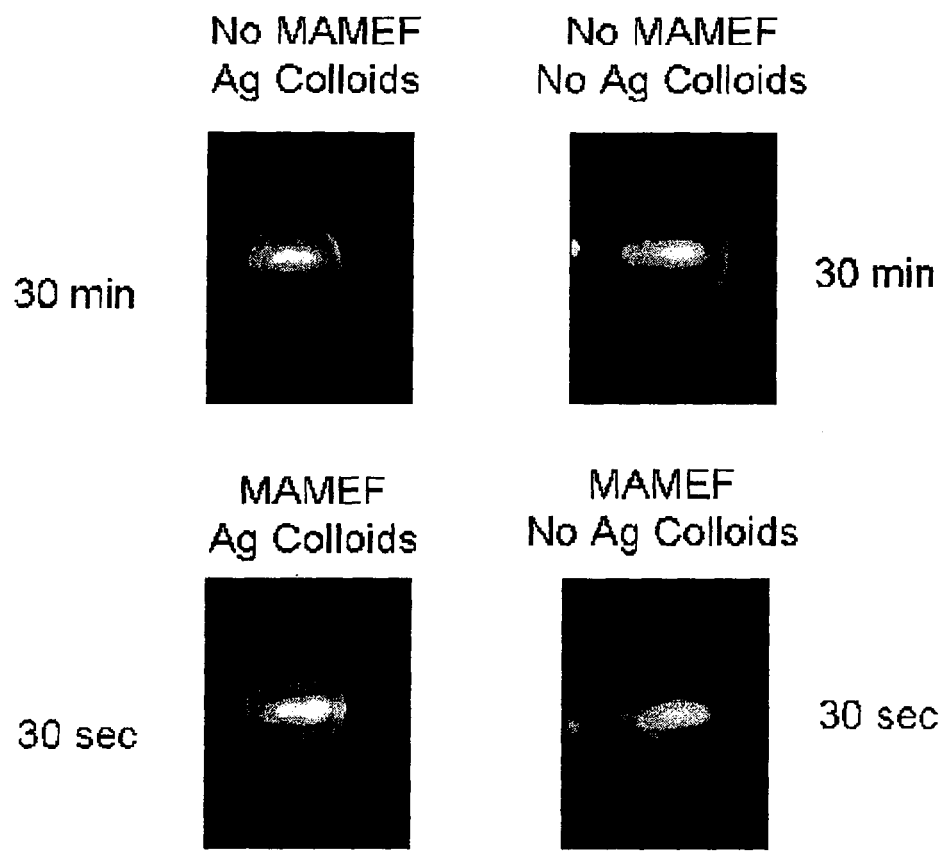
FIG. 25 shows photographs of actual HTS wells, with and without silver, before and after microwave heating. The photographs were taken through a long-pass filter with 473 nm TIR evanescent wave excitation.

The MAMEF comparison in the 96-well plates is also evident visually, as shown in the photographs of FIG. 25. The top left and right photographs visually compare the emission with and without silver, while bottom left and right show the effects of low power microwave heating, with and without silver colloids. Remarkably, by comparing both bottom-left with the photograph top right, the benefits of using the MAMEF technique can be clearly seen. All photographs were taken through a 500 nm razor edge filter with 473 nm evanescent wave excitation.

Figure 26:
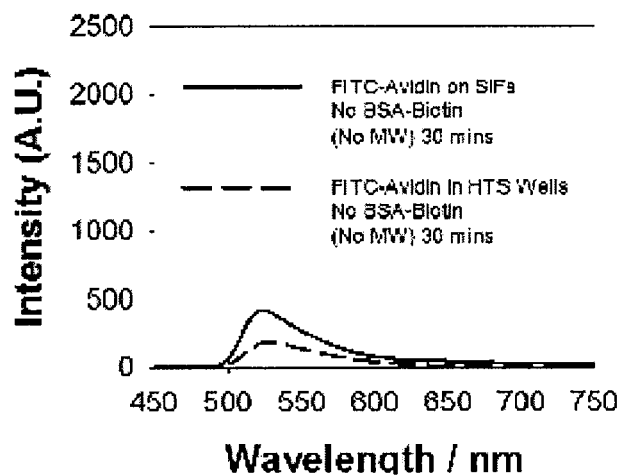
FIG. 26 shows the rates of control experiments of non-specific absorption of fluorescein-avidin to bare and silvered surfaces after 30 minutes incubation (Top), 30 seconds incubation (Middle), and after 30 seconds low power microwave heating (Bottom). The well bottoms were not coated with Biotinylated-BSA.
Figure 26:
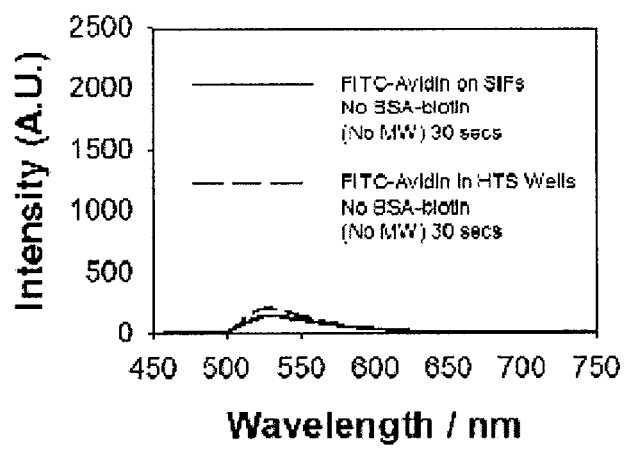
Figure 26:
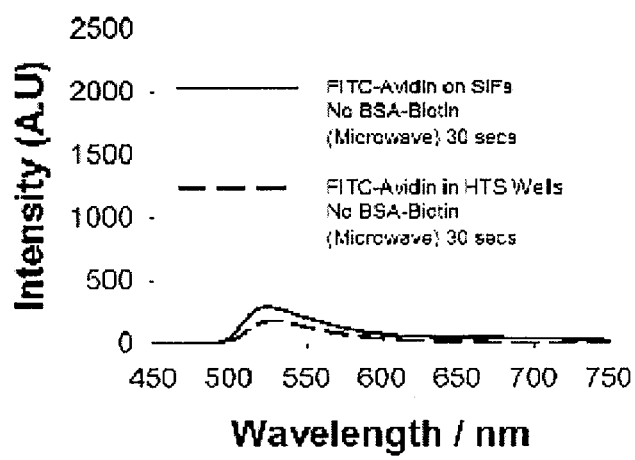

It was questioned if the use of low power microwaves in HTS well formats indeed increased the rate of non-specific absorption in the present model assay. In these experiments, the well bottoms were not pre-coated with biotinylated-BSA as is the case in the model assays shown in FIGS. 22, 23 and 24. From FIG. 26, (top) it can be seen that after 30 minute incubation in the wells with FITC-Avidin, followed by a washing step, fluorescein emission was evident, more so on the silvered as compared to the unsilvered well bottom, although the extent of absorption was much smaller than the actual assay shown in FIG. 23. Interestingly, a significantly large portion of the non-specific absorption occurred in the first 30 seconds of room temperature incubation, FIG. 26 middle. After low power microwave heating for 30 seconds, FIG. 26 bottom, similar fluorescence intensity was observed as compared to just 30 seconds room temperature incubation, c.f. FIG. 26 middle and bottom. This suggests that low power microwaves do not further accelerate non-specific absorption, beyond that normally present in this assay system.

In addition to traditional fluorescence photostability, the effects of low power microwave heating on the emission intensity of the fluorescein assay was investigated, where the assay was initially incubated for 30 minutes at room temperature. After this time, the assay was microwave heated in 5 second cumulative increments up to 1 minute, the fluorescence intensity measured at 530 nm after 473 nm excitation. After 1 minute of total heating and re-excitation, no change in the emission signal intensity was evident, indicating that low power microwaves do not perturb fluorescein fluorescence. Interestingly, under the conditions employed with this assay, it took greater than 5 minutes microwave heating to completely dry multiple plate well assays, up until which point, both the fluorescein emission spectra and peak intensity remained mostly constant.

Importantly, the low power microwaves employed here do not perturb the silvered surfaces and do not produce "arcing" which is commonly observed for larger metallic objects in microwave cavities.[58] The microwaves do not perturb the silver nanostructures, but simply increase the mass transport of protein to the plate well-bottoms. Further, low power microwaves provide for effective rapid heating of the assays, producing identical final fluorescence intensities as compared to longer room temperature incubation.

Further, the silver-enhanced evanescent field mode of excitation localizes the excitation volume in close proximity to the silver nanostructures. This eliminates the need for assay washing steps. In this regard the assay shown in FIG. 23, was shown to have almost identical spectral characteristics and intensities, with or without a washing step.

Although the invention has been described with respect to specific embodiments, the details are not to be construed as limitations, for it will become apparent that various embodiments, changes and modifications may be resorted to without departing from the spirit and scope thereof, and it is understood that such equivalent embodiments are intended to be included within the scope of the invention.

REFERENCES

The contents of all cited references are hereby incorporated by reference herein for all purposes.
(1) Bange A.; Halsall, H. B.; Heineman, W. R. Biosensors and Bioelectronics 2005, 20 (12), 2488-2503.
(2) Hemmilam L. A. *Applications if Fluorescence in Immunoassays*, John Wileys an Sons, New York, 1992.
(3) Van dyke, K.; Van Dyke, R. (Eds.), *Luminescence Immunoassay and Molecular Applications*, CRC Press, Boca Raton, Fla., 1990.
(4) Ozinkas, A. J. Principles of Fluorescence Immunoassay, in *Topics in Fluorescence Spectroscopy*, Volume 4, Lakowicz, J. R. (Ed.), Plenum Press, New York, 1994.
(5) Gosling, J. P. *Clin. Chem.* 1990, 36, 1408-1427.
(6) Davidson, R. S.; Hilchenbach, M. M. *Photocem. Photobiol.* 1990, 52, 431-438.
(7) Vo-Dinh, T.; Sepaniak, M. J.; Griffin, G. D.; Alarie, J. P. *Immunosensors* 1993, 3, 85-92.
(8) Schweitzer, B.; Kingsmore, S. F. Current Opinion in Biotechnology 2002, 13, 14-19.
(9) Lovgren, T.; Hemmila, I.; Petterson, K.; Halonen, P. Time-Resolved Fluorometry in Immunoassay, in *Alternative Immunoassays*, Collins, W. P. (Ed.), John Wileys an Sons, New York, 1985.
(10) Diamendis, E. P. *Clin. Chem.* 1988, 21, 139-150.
(11) Lovgren, T.; Petterson, K. Time-Resolved Fluoroimmunoassay; Advantages and Limitations, in *Luminescence Immunoassay and Molecular Applications*, CRC Press, Boca Raton, Fla., 1990.
(12) Khosravi, M.; Diamendis, E. P. *Clin. Chem.* 1987, 33, 1993-1999.
(13) Soini, E. Pulsed light, Time-Resolved Fluorometric Immunoassay, in *Monoclobal Antibodies and New Trends in Immunoassays*, Bizollon, C. A. (Ed), Elsevier Science Publishers, New York, 1984.
(14) Ullman, E. F.; Schwarzberg, M.; Rubenstein K. E. *J. Biol. Chem.* 1976, 251, 4172-4178.
(15) Ozinkas, A. J.; Malak, H.; Jaoshi, J.; Szmacinski, H.; Britz, J.; Thompson, R. B. Koen, P. A. Lakowicz, J. R. *Anal. Biochem.* 1993, 213, 264-270.
(16) Lakowicz, J. R; Ozinkas, A. J.; Thompson, R. B. *Sensors and Actuators.* 1993, 12, 65-70.
(17) Dandliker, W. B.; Saussure, V. A. *Immunochemistry* 1970, 7, 799-828.
(18) Spencer, R. D.; Toledo, F. B.; Williams, B. T.; Yoss, N. L. *Clin. Chem.* 1973, 19, 838-844.
(19) Aslan, K.; Gryczynski I.; Malicka J.; Matveeva E.; Lakowicz, J. R.; Geddes, C. D. Current Opinion in Biotechnology, 2005, 16(1), 55-62.
(20) Geddes, C. D.; Aslan, K.; Gryczynski, I.; Malicka, J.; Lakowicz, J. R., In *Review Chapter for Annual Reviews in Fluorescence 2004*, Geddes, C. D.; Lakowicz, J. R., Eds; Kluwer Academic/Plenum Publishers, New York, USA, 2004; pp. 365-401.
(21) Geddes, C. D.; Aslan, K., Gryczynski, I.; Malicka, J.; and Lakowicz, J. R. In *Topics in Fluorescence in Fluorescence Spectroscopy*, Geddes, C. D.; Lakowicz, J. R., Eds; Kluwer Academic/Plenum Publishers, New York, USA, 2005; pp. 401-448.
(22) Lakowicz, J. R. *Anal. Biochem.* 2001, 298, 1-24.
(23) Lakowicz, J. R.; Shen, Y.; D'Auria, S.; Malicka, J.; Fang, J.; Grcyzynski, Z.; Gryczynski, I. *Anal. Biochem.* 2002, 301, 261-277.
(24) Lakowicz J. R.; Shen Y.; Gryczynski Z.; D'Auria S.; Gryczynski I. *Biochem Biophys Res Com.* 2001, 286, 875-879.
(25) Malicka J.; Gryczynski I.; Lakowicz J. R. *Biochem and Biophys Res Com.* 2003, 306, 213-218.
(26) Lakowicz J. R.; Malicka J.; D'Auria S.; Gryczynski I; *Anal Biochem.* 2003, 320, 13-20.
(27) Aslan, K.; Lakowicz, J. R.; Szmacinski, H.; Geddes, C. D. *J. Fluoresc.* 2005, 15(1), 37-40.
(28) Malicka, J.; Gryczynski, I.; Geddes, C. D.; Lakowicz, J. R. *J. Biomed. Opt.* 2003, 8(3), 472-478.
(29) Geddes, C. D.; Cao, H.; Gryczynski, I.; Gryczynski, Z.; Fang, J.; Lakowicz, J. R. *J. Phys. Chem. A* 2003, 107(18), 3443.
(30) Aslan, K.; Lakowicz, J. R.; Geddes, C. D. *J. Phys. Chem. B.* 2005, 109, 6247-6251.
(31) Aslan, K.; Leonenko, Z.; Lakowicz, J. R.; Geddes, C. D.; *J. Phys. Chem. B.* 2005, 109(8), 3157-3162.

(32) Parfenov, A.; Gryczynski, I.; Malicka, J.; Geddes, C. D.; Lakowicz, J. R. *J. Phys. Chem. B.* 2003, 107(34), 8829-8833.
(33) Geddes C. D.; Parfenov, A.; Lakowicz, J. R. *Applied Spectroscopy* 2003, 57(5), 526-531.
(34) Geddes, C. D.; Parfenov, A.; Roll, D.; Fang, J.; Lakowicz, J. R. *Langmuir,* 2003, 19(15), 6236-6241.
(35) Aslan, K.; Badugu, R.; Lakowicz, J. R.; Geddes, C. D. *J. Fluoresc.* 2005, 15(2), 99-104.
(36) Geddes, C. D.; Parfenov, A.; Roll, D.; Gryczynski, I.; Malicka, J.; Lakowicz, J. R. *Spectrochimica Acta Part A,* 2004, 60(8-9), 1977-1982.
(37) Geddes C. D.; Lakowicz J. R. *J Fluoresc.* 2002, 12(2), 121-129.
(38) Geddes, C. D.; Gryczynski, I.; Malicka, J.; Gryczynski, Z.; Lakowicz, J. R. *Photonics Seectra,* 38 (2): 92+ February 2004.
(39) Lakowicz, J. R. *Analytical Biochemistry* 2004, 324 (2): 153-169.
(40) Lakowicz, J. R. *Principles of Fluorescence Spectroscopy*, Kluwer, New York, 1999.
(41) Matveeva, E.; Gryczynski Z.; Malicka, J.; Gryczynski, I.; Lakowicz, J. R. *Analytical Biochemistry* 2004, 334 (2): 303-311.
(42) Sridar, V. *Current Science* 1998, 74 (5): 446-450.
(43) Caddick, S. *Tetrahedron* 1995, 51, 10403-10432.
(44) Sridar V. *Indian Journal Of Chemistry Section B-Organic Chemistry Including Medicinal Chemistry* 1997, 36 (1): 86-87.
(45) Varma, R. S. *Advances in Green chemistry: Chemical Synthesis using Microwave Irradiation*, Astrazeneca Research Foundation, India, Banglore, 2002.
(46) Lin, J. C.; Yuan, P. M. K.; Jung, D. T. *Bioelectrochemistry and Bioenergetics* 1998, 47(2): 259-264.
(47) Akins, R. E.; Tuan, R, S. *Molecular Biotechnology* 1995, 4 (1): 17-24.
(48) Rhodes, A.; Jasani, B.; Balaton, A. J.; Barnes, D. M.; Anderson, E.; Bobrow, L. G.; Miller, K. D. *American Journal of Clinical Pathology* 2001, 115 (1): 44-58.
(49) Van Triest, B.; Loftus, B. M.; Pinedo, H. M.; Backus, H. H. J.; Schoenmakers, P.; Telleman F. *Journal of Histochemistry and Cytochemistry* 2000, 48 (6): 755-760.
(50) Croppo, G. P.; Visvesvara, G. S.; Leitch, G. J.; Wallace, S.; Schwartz, D. A. *Archives of Pathology and Laboratory Medicine* 1998, 122 (2): 182-186.
(51) Philippova T. M.; Novoselov, V. I.; Alekseev, S. I. *Bioelectromagnetics* 1994, 15 (3): 183-192.
(52) Roy, I.; Gupta, M. N. *Current Science* 2003, 85(12), 1685-1693.
(53) Bismuto, E.; Mancinelli, F; d'Ambrosio, G.; Massa, R. *Eur. Biophy. J.* 2003, 32, 628-634.
(54) Porcelli, M.; Cacciapuoti, G.; Fusco, S.; Massa, R.; d'Ambrosio, G.; Bertoldo, C.; DeRosa, M.; Zappia, V. *Febs Letters* 1997, 402 (2-3): 102-106.
(55) Adam, D. *Nature* 2003, 421, 571-572.
(56) Whittaker, A. G.; Mingos, D. M. P. *J. Chem. Soc. Dalton Trans.* 1995, 12, 2073-2079.
(57) Kappe, C. O. *Curr. Opin. Chem. Biol.* 2002, 6, 314-320.
(58) Whittaker, A. G.; Mingos, D. M. P. *J. Chem. Soc. Dalton Trans.* 1993, 16, 2541-2543.
(59) Technology Vision 2020, The US Chemical Industry, December 1996.
(60) Chen, S. T. Sookheo, B. Phutrahul, S. Wang, K. T. Enzymes in Nonaquoeous Solvents: Applications in Carbohydrate and Peptide Preparation, in *Enzymes in Nonaquoeous Solvents*, Vulfson E. N.; Halliog P. J.; Bolland, H. L. (Eds.), Humana Press, New Jersey, 2001, pp. 373-400.
(61) Micheva, K. D.; Holz, R. W.; Smith, S. J. *J. Cell Biol.* 2001, 154, 355-368.
(62) Petrali, J. P.; Mills K. R. *Micro Microanalysis,* 1998, 114-115.
(63) Link, S.; El-Sayed, M. A., *J. Phys. Chem. B.,* 1999, 103, 8410-8426.
(64) Kreibig, U.; Genzel, L. *Surface Science* 1985, 156, 678-700.
(65) Gao, F.; Lu, Q.; Komarneni, S. *Chem. Mater.* 2005; 17(4); 856-860.
(66) Liu, F-K.; Chang, Y-C.; Huang, P-W.; Ko, F-H.; Chu, T-C. *Chem. Lett.* 2004, 33(8), 1050-1051.
(67) Liu, F-K.; Huang, P-W.; Chu, T-C.; Ko, F-H. *Materials Letters* 2005, 59 (8-9), 940-944.
(68) Liu, F-K.; Huang, P-W.; Chang, Y-C.; Ko, C-J.; Ko, F-H.; Chu, T-C. *J. Crystal Growth,* 2005, 273 (3-4): 439-445.
(69) Liu, F-K.; Huang, P-W.; Chang, Y-C.; Ko, F-H.; Chu, T-C. *J. Mater. Res.* 2004, 19 (2): 469-473.
(70) Aslan, K.; Lakowicz, J. R.; Geddes, C. D. *Analytical Biochemistry* (submitted).
(71) Green, N. M. *Adv. Protein Chem.* 1975, 29, 85-133.
(72) Wilchek, M.; Bayer, E. A. *Anal. Biochem.* 1998, 171, 1-6.
(73) Wilchek, M.; Bayer, E. A. *Methods of Enzymology*; Vol. 184, Academic Press, San Diego. 1990.
(74) Baziard Y.; Breton, S.; Toutain, S.; Gourdenne, A. *Eur. Polym. J.* 1988, 24, 521-526.
(75) Axelrod, D., Hellen, E. H. and Fulbright, R. M. Total internal reflection fluorescence, in *Topics in Fluorescence Spectroscopy*, Vol. 3: *Biochemical applications*, Lakowicz J. R., (Ed.), Plenum Press, New York, 1992 pp. 289-343.
(76) Sokolov, K.; Chumanov, G.; Cotton, T. M. *Anal. Chem.* 1998, 70, 3898-3905.
(77) Chicoine, L.; Webster, P. *Micro Res. Tech.* 1998, 42, 24-32.
(78) Madden, V. J. *Micro Microanalysis* 4, 1998, 854-855.
(79) Rangell, L. K.; Keller, G. A. *J. Histochem. Cytochem.* 2000, 28, 1153-1160.
(80) Schichnes, D.; Nemson, J.; Sohlberg, L.; Ruzin, S. E. *Micro Microanalysis* 4, 1999, 491-496.
(81) Ressner, U. A.; Crumrine, O. A.; Nau, P.; Elias, P. M. *Histochem. J.* 1997, 29, 387-392.
(82) Schray, C. L.; Metz, A. L.; Gough, A. W. *Histologic* 2002, 35(1), 7-12.
(83) Rivas L., Sanchez-Cortes S., Garcia-Ramos J. V. and Morcillo G., (2001) *Langmuir,* 17(3), 574-577 (2001).
(84) Shirtcliffe N., Nickel U. and Schneider S., *J. Colloid Interface Sci.,* 211(1), 122-129 (1999);
(85) Pastoriza-Santos I., and Liz-Marzan L. M., *Pure Appl. Chem.,* 72(1-2), 83-90 (2000);
(86) Pastoriza-Santos I., Serra-Rodriquez C. and Liz-Marzan L. M., *J. Colloid Interface Sci.,* 221(2), 236-241 (2000);
(87) Bright R. Musick M. D. and Natan M. J., *Langmuir,* 14(20), 5695-5701 (1998);
(88) Ni F. and Cotton T. M., *Anal. Chem.,* 58(14), 3159-5163 (1986).
(89) Krelbig U., Gartz M. and Hilger A, *Ber. Bunsenges, Phys. Chem.,* 101(11), 1593-1604. (1997).
(90) Freeman R. G., Grabar K. C., Allison K. J., Bright R. M., Davis J. A., Guthrie A. P., Hommer M. B., Jackson M. A., Smith P. C., Walter D. G. and Natan M. J., *Science,* 267, 1629-1632 (1995).
(91) Grabar K. C., Freeman R. G., Hommer M. B. and Natan M. J., *Anal. Chem.,* 67, 735-743 (1995).
(92) Copending PCT International Application No. PCT/US 2005/039498.
(93) Whittaker, D. M. P. Mingos (1993)., *J. Chem. Soc. Dalton Trans.* 16, 2541-2543.

What is claimed is:

1. A system for shortening the time required to detect or measure the presence of a target molecule in a sample, the system comprising:
   a metallic material, wherein the metallic material is shaped as particles, nanostructures, islands or colloids;
   a probe attached to the metallic material for binding with the target molecule in the sample;
   the sample suspected of containing the target molecule;
   a source of low power microwave energy that emits energy in the gigahertz frequency range in an amount sufficient to increase the kinetics of a chemical reaction involving at least the binding of the target molecule to the probe;
   a detecting molecule that binds to the target molecule and emits detectably energy when radiated with excitation energy;
   a source of excitation energy that emits in the UV to IR range for irradiating the detecting molecule; and
   a detection or measuring device to measure the emitted signal from the system.

2. The system according to claim 1, wherein the metallic material comprises silver or gold.

3. The system according to claim 1, wherein the low power microwave energy is from 30 mwatts to 200 watts.

4. The system according to claim 1, wherein the metallic material is positioned on a substrate.

5. The system according to claim 4, wherein the substrate is glass, quartz or a polymeric material.

6. The system according to claim 5, wherein the substrate is a polymeric well plate used in High Throughput Screening (HTS) comprising a multiplicity of wells, wherein the metallic material is positioned on at least the bottom of each of the multiplicity of wells.

7. The system according to claim 1, wherein the detecting molecule is an intrinsic fluorophore.

8. The system according to claim 1, wherein the detecting molecule is attached to an extrinsic fluorophore.

9. The system according to claim 1, wherein the metallic material is in the form of a three dimensional matrix, wherein metal particles are positioned on a surface of a porous substrate or the metal particles are embedded in the porous substrate.

10. The system according to claim 1, wherein the detecting molecule is positioned from the metallic material at a distance from about 4 nm to 20 nm.

11. The system according to claim 1, wherein the particles are triangular in shape.

12. A kit for detecting a target molecule in a sample, the kit comprising:
   a container comprising a layer of immobilized metal particles deposited on a substrate fabricated of a polymeric or quartz material, wherein an immobilized probe is connected to the metal particles and wherein the immobilized probe has an affinity for the target molecule;
   a detector molecule having an affinity for the target molecule, wherein the binding of the target molecule to both the immobilized probe and detector molecule causes the detector molecule to be positioned a sufficient distance from the immobilized metal particles to enhance emissions due to excitation by a radiation source;
   a source of microwave energy that emits energy in the gigahertz frequency range and can deliver low power microwave energy in a range from 30 mwatts to 200 watts; and
   a detection device.

13. A kit according to claim 12, wherein the particles are triangular in shape.

* * * * *